(12) United States Patent
Norbeck et al.

(10) Patent No.: US 12,293,818 B2
(45) Date of Patent: May 6, 2025

(54) KIOSK TO DISPENSE MEDICATION SUCH AS MEDICINE FOR OPIOID ADDICTION

(71) Applicant: Opio Connect, Inc., Kalispell, MT (US)

(72) Inventors: Amber Olivia Norbeck, Kalispell, MT (US); Michael Pokorny, Kalispell, MT (US); Thomas Hoffmann, Mooresville, NC (US); Bradley Wayne Bauer, Salt Lake City, UT (US)

(73) Assignee: Opio Connect, Inc., Kalispell, MT (US)

( * ) Notice: Subject to any disclaimer, the term of this patent is extended or adjusted under 35 U.S.C. 154(b) by 411 days.

(21) Appl. No.: 17/891,941

(22) Filed: Aug. 19, 2022

(65) Prior Publication Data
US 2023/0062587 A1  Mar. 2, 2023

Related U.S. Application Data

(60) Provisional application No. 63/239,324, filed on Aug. 31, 2021.

(51) Int. Cl.
| | | |
|---|---|---|
| *G16H 20/13* | (2018.01) | |
| *A61J 1/03* | (2023.01) | |
| *G16H 80/00* | (2018.01) | |

(52) U.S. Cl.
CPC .............. *G16H 20/13* (2018.01); *A61J 1/03* (2013.01); *G16H 80/00* (2018.01); *A61J 2200/40* (2013.01); *A61J 2200/50* (2013.01); *A61J 2200/70* (2013.01)

(58) Field of Classification Search
CPC ........ G16H 20/13; G16H 80/00; G16H 10/60; G16H 40/67; A61J 1/03; A61J 2200/40; A61J 2200/50; A61J 2200/70; A61J 2205/10; A61J 2205/60; A61J 1/065
See application file for complete search history.

(56) References Cited

U.S. PATENT DOCUMENTS

| | | | |
|---|---|---|---|
| 11,830,616 B1 * | 11/2023 | Solie .................... | A61B 5/0077 |
| 11,978,552 B2 * | 5/2024 | Solie .................... | G06Q 20/18 |
| 12,119,112 B1 * | 10/2024 | Solie .................... | A61B 5/6888 |

(Continued)

*Primary Examiner* — Michael Collins
(74) *Attorney, Agent, or Firm* — Seed IP Law Group LLP

(57) ABSTRACT

The present disclosure is directed to embodiments of a kiosk including a chassis having a patient compartment and a medication compartment. A patient does not have access to the medication compartment in the patient compartment. A dispense structure extends from the patient compartment to the medication compartment such that a dosage of medication may be dispensed to the patient when within the patient compartment. After the medication is dispensed to the patient, a medical professional observes the patient ingest the medication through a video conference display within the patient compartment. A biometric scanner may be in electrical communication with a lock in mechanical cooperation with a door hingedly coupled to the chassis to limit access to the medication compartment. An insulated safe with an internal chamber wherein the internal chamber's temperature is regulated. A medication is stored within the internal chamber of the insulated safe at a selected temperature by regulating the temperature within the internal chamber of the insulated safe.

13 Claims, 13 Drawing Sheets

(56) References Cited

U.S. PATENT DOCUMENTS

| | | | |
|---|---|---|---|
| 2005/0192705 A1* | 9/2005 | Pinney | G07F 11/62 700/217 |
| 2012/0179479 A1* | 7/2012 | Waterson | G16H 80/00 705/2 |
| 2014/0095196 A1* | 4/2014 | Waterson | G16H 10/40 705/2 |
| 2014/0165614 A1* | 6/2014 | Manning | F25D 29/00 62/62 |
| 2020/0168329 A1* | 5/2020 | Solie | A61B 5/7465 |
| 2021/0035400 A1* | 2/2021 | Flynn | G07F 11/54 |

\* cited by examiner

KIOSK TO DISPENSE MEDICATION SUCH AS MEDICINE FOR OPIOID ADDICTION

BACKGROUND

Technical Field

The present disclosure is directed to a kiosk including a medication compartment and a patient compartment with limited or restricted access to the medication compartment.

Description of the Related Art

In the United States, it is estimated that 130 people die every day, nearly 50,000 deaths per year, from overdoses on opioids. In 2017, an estimated 1.7 million people suffered from opioid use disorder (OUD) related to prescription opioids, and 652,000 people suffered from heroin use disorder.

The misuse of prescription opioids alone, not including illicit street opioids, costs the U.S. $800 billion per year. The White House Council on Economic Advisers estimated that in 2015, the total economic cost of the opioid crisis in the U.S. was $504 billion. That equals $1.38 billion a day. Fatality costs comprise over 85 percent of total costs, highlighting the crucial role played by mortality risk valuations when assessing the costs of this epidemic.

Generally, medicine is provided to a patient at medical clinics, pharmacies, or other similar or like medical practices. The patient obtains their treatment at these locations by interacting in-person with a trained nurse, pharmacist, or medical professional to obtain the patient's medication. For example, when the patient is beginning their participation in Opioid Treatment Program (OTP), the patient will usually need to travel to the medical clinic or pharmacy approximately once every 24-hour period (e.g., day) to obtain and ingest a dosage of methadone, which is an opioid addiction treatment medication or drug. However, these locations usually have limited working hours in which the patient must be readily available to travel to these locations to obtain and ingest their dosage of methadone. These limited working hours of these locations may cause difficulty for the patient to obtain their dosage of methadone on a regular basis due to the patient needing to balance work, unexpected life events (e.g., emergencies, children out of school, etc.), or other responsibilities or unplanned situations along with obtaining their medication to treat an opioid addiction.

The two primary medications used to treat opioid use disorder (OUD) are methadone and buprenorphine. Both medications are opioids, but they have vastly different regulatory controls. Methadone treatment for addiction is tightly regulated by federal guidelines and must be performed at a certified OTP clinic. Methadone initiation requires observed dosing for at least six days per week. There are very specific regulations on the maximum take home doses which is dependent on the duration in the treatment program. As discussed earlier, many times, OTP clinics or medical facilities only have limited working hours. For example, OTP clinics or medical facilities may only be open a few hours a day making accessibility difficult, and many states have a very limited number of OTP certified clinics or medical facilities. In short, while the use of methadone to address the opioid crisis is effective, the accessibility to the methadone on a regular basis is of limited effectiveness at least due to OTP's limited working hours.

Generally, these medical clinics, pharmacies, or similar or like medical practices are located in more urban environments such as cities or suburban areas where a greater number of medical professionals are readily present due to the greater population in these areas. Whereas in rural or underserved locations there generally are fewer medical clinics, pharmacies, or other similar or like medical practices at which patients may readily obtain their dosage of methadone or some other similar for addiction treatment. For example, a patient located in a rural or underserved location may need to travel a significantly greater distance as compared to another patient in an urban or suburban area. Similarly, the patient located in the rural locations may have more difficulty due to limited access to public transportation such as subways, trains, buses, shuttles, etc., that the patient may readily access to take advantage of to obtain their treatment on regular and scheduled basis.

Generally, there are a greater number of underserved locations. For example, about 22% of counties in the United States have access to methadone to treat patients with an opioid addiction.

When the patient is taking their treatment such as the dosage of methadone when participating in an OTP, a nurse, pharmacist, or some other like or similar medical profession must observe the patient taking the medication to avoid diversion of the medication. This observed dose, which is federally mandated, is to reduce the likelihood of diversion (e.g., the patient not taking the medication to sell to another individual) by the patient. This observed dose requirement means the patient must organize their work and life around the limited working hours of the medical clinics or pharmacies to obtain their treatment on a regular or scheduled basis.

The above factors and federally mandate requirements of observed doses for certain addiction treatments such as OTPs to avoid diversion may make it difficult for a patient in a rural or underserved area to participate in an OTP to overcome an opioid addiction. In view of the above factors and the federally mandated observed doses, the medical industry is looking for ways to increase and improve access to doses of medication (e.g., doses of methadone) to treat addictions such as opioid addictions or other similar or like ailments that satisfy the factors as discussed above such as providing interaction between patients and medical professionals (e.g., observed doses), providing proper storage of the doses of medication(s) to avoid early expiration, and providing proper security when storing the doses of medication. It will be readily appreciated that the list of above factors is not a complete and full list of factors that may be of interest to the medical industry when looking for ways to increase and improve access to doses of medication to treat an opioid addiction or other ailments.

BRIEF SUMMARY

The present disclosure is directed to a kiosk to provide patients access to doses of medication (e.g., pharmaceutical agent) for treating ailments such as an opioid addiction. In at least one embodiment, the kiosk includes a chassis having a medication compartment and a patient compartment separate from the medication compartment and having limited access to the medication compartment. A safe is within the medication compartment and includes an internal chamber in which doses of medication (e.g., strips of buprenorphine, doses of methadone in individual containers such as medication bottles, medication vials, or other similar or like medication containers or other similar or like medications) are stored. The safe is insulated to assist in maintaining the doses of medication at a selected temperature for storage to avoid early expiration or deterioration of the medication or for tracking the medication by a thermal imager (e.g., thermal imaging camera) to confirm ingestion of the medication by the patient to avoid diversion of the medication. The internal chamber is maintained at the selected temperature by a temperature adjustment module within the internal chamber of the safe, and the temperature adjustment module is in fluid communication with an environment external the safe and the chassis.

A dispense structure extends from the internal chamber to the patient compartment such that doses of medication may be transported from the medication compartment to the patient compartment. The dispense structure may be a hollow structure having a reception opening at a first end accessible in the medication compartment and a dispense opening at a second end accessible in the patient compartment. There may be an openable seal that prevents the cooler air from the internal chamber leaking into the patient compartment when not delivering a medication.

A medication container storage case is within the internal chamber of the safe such that individual ones of medication containers (e.g., medication bottles, medication vials, etc.) containing doses of medication are stored within the medication container storage case. A manipulator (e.g., pneumatic robotic arm) is within the internal chamber. The manipulator may pick up individual ones of the medication containers and place them within the reception opening at the first end of the dispense structure such that the medication container may be accessed through the dispense opening at the second end of the dispense structure. For example, when the manipulator arm places the medication container containing the dosage of medication within the reception opening, a patient may then grab the medication container through the dispense opening, open the medication container, and take their dosage of medication while being observed by a medical professional through a video conference display within the patient compartment to avoid diversion of the medication through an observed dose.

The video conference display is within the patient compartment such that a medical professional (e.g., nurse, pharmacist, doctor, or some other similar or like trained medical professional or certified medical professional) may interact with the patient without having to be in-person. The video conference display may include a camera to monitor the patient to confirm ingestion of the patient's dosage of medication as well as reduce the likelihood of diversion of the dosage of medication by the patient.

A first biometric scanner is accessible at an external surface of the chassis. The first biometric scanner may be in electrical communication with a first lock, which is in mechanical cooperation with a medication compartment door coupled to the chassis, and a second lock, which is in mechanical cooperation with safe door of the safe. The first biometric scanner may be utilized to unlock the first lock to access the medication compartment through the medication compartment door, and may be utilized to unlock the second lock to access the internal chamber of the safe through the safe door.

A first surveillance camera is within the internal chamber to monitor the internal chamber of the safe. For example, the first surveillance camera may readily monitor and record the internal chamber 24/7 to keep a record of who accesses the internal chamber to avoid misappropriation or unauthorized acquisition of medication within the internal chamber. In at least one situation, for example, the surveillance camera may record a maintenance employee when the maintenance employee accesses the internal chamber to perform maintenance on components within the internal chamber.

The video conference display may include a thermal imager, which may be a thermal image camera, to monitor whether the patient has ingested the medication to avoid diversion of the medication. Since the medication stored within the medication chamber is at the selected temperature, the thermal image camera tracks the ingestion of the medication by the patient. For example, the medication may be stored at the selected temperature that is colder than the ambient temperature within the patient compartment, the thermal image camera may track the medication (e.g., pill, liquid, etc.) by outputting a heat map that is visible to the medical professional in which the medication is represented by a blue color. Shortly after the patient has inserted the medication into their mouth and ingested (e.g., swallowed) the medication, the medical professional may request that the patient open their mouth and lift their tongue to confirm that the medication was ingested by the patient by confirming no blue color remains within the mouth of the patient or underneath the tongue's patient. Similarly, the thermal image camera may be sensitive enough to detect the medication at the selected medication even when the patient's mouth is closed to monitor ingestion of the medication at the selected temperature.

BRIEF DESCRIPTION OF THE SEVERAL VIEWS OF THE DRAWINGS

For a better understanding of the embodiments, reference will now be made by way of example to the accompanying drawings. In the drawings, identical reference numbers identify the same or similar elements or acts unless the context indicates otherwise. The sizes and relative proportions of the elements in the drawings are not necessarily drawn to scale. For example, some of these elements may be enlarged and positioned to improve drawing legibility.

DETAILED DESCRIPTION

Figure 1A:
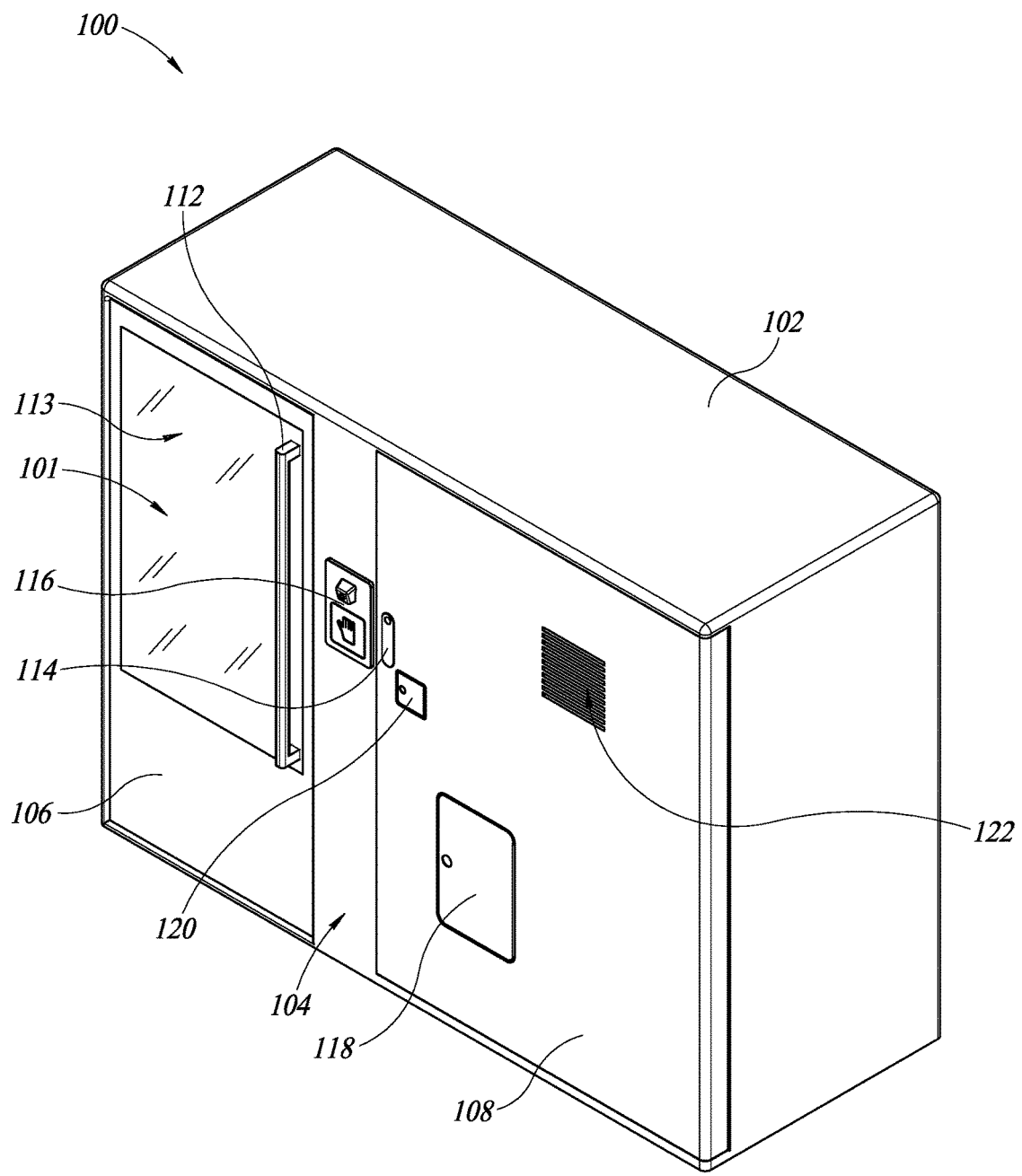
FIG. 1A is a perspective view of an embodiment of a kiosk of the present disclosure.

In the following description, certain specific details are set forth in order to provide a thorough understanding of various embodiments of the disclosure. However, one skilled in the art will understand that the disclosure may be practiced without these specific details. In other instances, well-known structures associated with electronic components, medication, and kiosks have not been described in detail to avoid unnecessarily obscuring the descriptions of the embodiments of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

The use of ordinals such as first, second, third, etc., does not necessarily imply a ranked sense of order, but rather may only distinguish between multiple instances of an act or a similar structure or material.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms "left" and "right," are used for only discussion purposes based on the orientation of the components in the discussion of the Figures in the present disclosure as follows. These terms are not limiting as the possible positions explicitly disclosed, implicitly disclosed, or inherently disclosed in the present disclosure.

The term "substantially" is used to clarify that there may be slight differences and variation when a package is manufactured in the real world, as nothing can be made perfectly equal or perfectly the same. In other words, "substantially" means and represents that there may be some slight variation in actual practice and instead is made or manufactured within selected tolerances.

As used in this specification and the appended claims, the singular forms "a," "an," and "the" include plural referents unless the content clearly dictates otherwise.

While various embodiments are shown and described with respect to kiosks to dispense medication to a patient, it will be readily appreciated that embodiments of the present disclosure are not limited thereto. In various embodiments, the structures, devices, methods and the like described herein may be embodied in or otherwise utilized in any suitable type or form to dispense any number of medications to patients.

Buprenorphine significantly reduces cravings, illicit opioid use, and mortality, as well as improves psychosocial outcomes in patients with opioid use disorder (OUD). Medication assisted treatment with opioid agonist therapy, such as buprenorphine, has been shown to decrease mortality by approximately 50% among persons with OUD. Medication-based treatment with buprenorphine has also been shown to decrease healthcare costs by $20,000 per patient annually, when adherence is 80% or greater. It is the ideal medication to begin in the emergency department or after opioid overdoses. Unfortunately, only 20% of people with OUD are in medication-based treatment.

The worsening opioid epidemic has led to an increase in prescribing of this medication, in 2012, there were 9 million prescriptions for SUBOXONE®, accounting for a $1.5 billion market share. Buprenorphine is highly effective when taken appropriately as prescribed, however, without any controls in place when prescribing a significant quantity of opioids to a person with OUD, the consequence has been a drastic increase in diversion and subsequent new buprenorphine addiction. SAMHSA (Substance Abuse and Mental Health Services Administration) reported that buprenorphine was the highest misused prescription opioid in 2018, accounting for 718,000 cases (28.3%). Rural areas with lack of treatment for OUD have increased rates of diversion of buprenorphine as well as higher rates of opioid overdose deaths.

A healthcare provider generally selects frequency and dose based on a patient's level of addiction, their body size and composition, and progress through their treatment plan, among other things. As an example, some patients may receive a dosing frequency of a dose of medication every twelve hours. In some instances the dosing window may be more frequent than twelve hours. In some instances the dosing window may be less frequent than twelve hours. It is noted that different states and counties have different rules and regulations regarding acceptable availability, as such, the kiosks of the present disclosure can be programmed to honor local rules and regulations accordingly.

The present disclosure is directed to embodiments of a kiosk that provides access to doses of medication (e.g., pharmaceutical agents) to a patient to treat an ailment or to treat an addiction. For example, the patient may be participating in an opioid treatment program (OTP). The kiosk may be located to provide rural or underserved areas additional access to medication treatments to treat an ailment of the patient or to provide the patient access to a dose/dosage of medication when participating in a treatment program such as an OTP. Embodiments of kiosks of the present disclosure include several components such that a medical professional may readily interact with the patient without having to be in-person to improve access to their medication while reducing the likelihood of diversion of the medication by the patient and confirm ingestion of the medication by the patient. Embodiments of the kiosk of the present disclosure include components to maintain doses/dosages of medication at a selected temperature to reduce the likelihood of the dosages of medication expiring before their expiration date.

In at least one embodiment, the kiosk includes a chassis having a medication compartment and a patient compartment separate from the medication compartment. The patient compartment being limited in access to the medication compartment. A safe within the medication compartment includes an internal chamber in which doses of medication (e.g., doses of methadone in individual containers such as medication bottles or medication vials) are stored. The safe is insulated to assist in maintaining the doses of medication at a selected temperature for storage of the doses of medication to avoid expiration or deterioration of the medication before an expiration date of the medication. The internal chamber is maintained at the selected temperature by a temperature adjustment module within the internal chamber of the safe, and the temperature adjustment module is in fluid communication with an environment external to the safe and the chassis. This may be a fan, an air conditioning system, or other air flow management device.

A dispense structure extends from the internal chamber to the patient compartment such that medication containers containing doses of medication may be transported from the medication compartment to the patient compartment. The dispense structure may be a hollow structure having a reception opening at a first end accessible in the medication compartment and a dispense opening at a second end accessible in the patient compartment.

A valve structure or insulation barrier may be present along and within the hollow structure of the dispense structure between the first end and the second end of the dispense structure. The valve structure or insulation barrier prevents cold air within the internal chamber of the safe passing through the reception opening into the hollow structure of the dispense structure and then entering the patient compartment through the dispense opening. In other words, the valve structure or insulation barrier limits the transfer of cold air in the internal chamber of the safe to the patient compartment through the dispense structure. The valve structure or insulation barrier is structured such that the medication containers containing doses of medication may readily pass by or through the valve structure or insulation barrier when being dispensed to an authorized patient.

A medication container storage case is within the internal chamber of the safe such that individual ones of medication containers (e.g., medication bottles, medication vials, etc.) containing doses of medication are stored within the medication container storage case. A manipulator (e.g., pneumatic robotic arm) is within the internal chamber. The manipulator picks up individual ones of the medication containers and places them within the reception opening at the first end of the dispense structure such that the medication container may be accessed through the dispense opening at the second end of the dispense structure. For example, when the manipulator places the medication container containing the dosage of medication within the reception opening, a patient may then grab the medication container to take their dosage of medication through the dispense opening.

A first biometric scanner is accessible at an external surface of the chassis. The first biometric scanner may be in electrical communication with a first lock, which is in mechanical cooperation with a medication compartment door coupled to the chassis, and a second lock, which is in mechanical cooperation with a door of the safe. The first biometric scanner may be utilized to unlock the first lock to access the medication compartment through the medication compartment door, and may be utilized to unlock the second lock to access the internal chamber of the safe through the door of the safe.

A first surveillance camera is within the internal chamber to monitor the internal chamber. For example, the first surveillance camera may readily monitor and record the internal chamber to keep a record of who accesses the internal chamber. In at least one situation, the surveillance camera may record a maintenance employee when the maintenance employee accesses the internal chamber to perform maintenance on components within the internal chamber. The internal camera may also be utilized for tracking delivery of a controlled substance from in the chamber, confirmed by a remote medical professional, and then delivered to an authorized patient in the patient compartment.

A video conference display is within the patient compartment such that a medical professional (e.g., nurse, pharmacist, doctor, or some other trained medical professional or certified medical professional) may interact with the patient without having to be in person. The video conference display may include a camera to monitor the patient to confirm ingestion of the patient's dosage of medication as well as reduce the likelihood of diversion of the dosage of medication by the patient.

FIG. 1A is a perspective view illustrating an embodiment of a kiosk 100 of the present disclosure. The kiosk includes a chassis or structure 102 having an external surface 104. A patient compartment 101 is in the chassis 102. The patient compartment 101 may be soundproofed such that a patient within the patient compartment 101 may not be heard by individuals outside of the kiosk 100. This allows for any discussion between a patient and a medical professional to remain confidential between the patient and the medical professional. For example, the patient compartment 101 may be lined with sound deadening panels that dampen out 25-decibels of sound such that a patient's conversation with a medical professional may not be heard outside of the kiosk 100.

A first door 106 and a second door 108 are coupled to the chassis 102. The first and second doors 106, 108 may be hingedly coupled to the chassis such that the first and second doors 106, 108 are opened and closed by rotating the first and second doors about respective hinges. The first door 106 provides access to the patient compartment 101 and may be referred to as a patient compartment door, whereas the second door 108 provides access to a medication compartment 110 within the chassis 102 and may be referred to as a medication compartment door.

The first door 106 has a first handle 112 to assist in opening and closing the first door 106. The first handle 112 may be a bar handle, a cantilever handle, a latch handle, or some other type of handle. An optional window 113 is in the first door 106 such that the patient compartment is readily visible when outside the kiosk. The window allows for an individual or patient who may have the intention to enter the patient compartment 101 of the kiosk 100 to be aware that another individual or patient may already be present within the patient compartment 101. The window may be different sizes. Alternatively, there may be an indicator on the door that provide an indication of occupancy. This could be electronic or physical, such as a latch indicator that rotates between occupied and available based on a position of the latch within the patient compartment.

The second door 108 includes a second handle 114 to assist in opening and closing the second door 108. The second handle 114 may be a latch handle, a bar handle, a cantilever handle, or some other type of handle.

While not readily visible, a first lock is present such that the first lock locks the second door 108 in the closed position. For example, in an embodiment, the first lock may be in mechanical cooperation with the second door 108 to lock the second door 108. In an alternative embodiment, the first lock may be in mechanical cooperation with the second handle 114 such that the second handle 114 is locked in place and may not be articulated to open up the second door 108.

The first lock may not be accessible from the outside of the chassis 102 of the kiosk 100. For example, in an embodiment of the kiosk 100, the first lock may be within the medication compartment 110 of the chassis 102 such that the first lock is not accessible from the outside of the chassis 102. In alternative embodiments of the kiosk 100, the first lock may be positioned at an alternative location that is not easily and readily accessible by an individual who may not have permission, certification, or approval to open the second door 108 of the kiosk 100. The first lock may be a mechanical lock, an electro-mechanical lock, or some other type of lock that denies or limits access to an individual without permission, certification, or approval to open the second door 108 to access the medication compartment 110.

A first biometric scanner 116 is accessible at the external surface 104 of the chassis 102. The first biometric scanner 116 is on the external surface 104 of the chassis 102, and may be a finger or hand print scanner, a facial identification scanner, a retinal scanner, or some other type of biometric scanner or some other combination of biometric scanners. Alternatively, if the first biometric scanner 116 is a combination of different types of biometric scanners, the first biometric scanner 116 may be a retinal and facial identification scanner, may be a fingerprint and retinal scanner, or may be some other combination of types of biometric scanners. The first biometric scanner 116 is in electrical communication with the first lock such that the first biometric scanner 116 may send an electrical signal to the first lock to unlock the first lock. Once the first lock is unlocked, the second door 108 may be opened. For example, if the first biometric scanner 116 is a finger print scanner, a maintenance employee may scan their finger print with the first biometric scanner 116, and, if the maintenance employee has proper approval, certification, or permission to open the second door 108, the first lock is unlocked such that the second door 108 may be opened to access the medication compartment 110.

A first hatch 118 is on the second door 108, and a second hatch 120 is on the second door 108. The first hatch 118 may provide limited access to a first drawer 132 behind the first hatch 118, and the second hatch 120 may provide limited access to a second drawer 136 behind the second hatch 120. The details of the functionality of the first and second hatches 118, 120, respectively, will be discussed in further detail with respect to FIG. 1I.

A plurality of vents 122 extend through the second door 108. The plurality of vents 122 are exhaust vents that are in fluid communication with a temperature adjustment module 130 within the medication compartment 110. The plurality of vents 122 allow the temperature adjustment module 130 to maintain a medication within the medication compartment at a selected (e.g., regulated) temperature to reduce the likelihood of early expiration of the medication. These vents could be on other surfaces of the kiosk such as the side surface adjacent to the door 108 or a rear surface that is opposite to the first surface 104.

When methadone is stored within the kiosk 100, the temperature adjustment module 130 may maintain or regulate the temperature within the internal chamber 128 ranging from 59-degrees Fahrenheit to 65-degrees Fahrenheit. However, if a different medication is stored within the internal chamber 128, the temperature adjustment module 130 may maintain or regulate the temperature within the internal chamber 128 at some other temperature to reduce the likelihood of early expiration or deterioration of the medication or medications stored within the internal chamber 128. The temperature adjustment module 130 includes a thermometer or other temperature sensor to monitor in real-time the temperature in a safe 124. The temperature adjustment module 130 either adjusts the temperature directly based on threshold temperatures set or transmits the information to a remote server via the cloud for remote monitoring and adjustment to maintain the threshold temperatures.

Figure 1B:
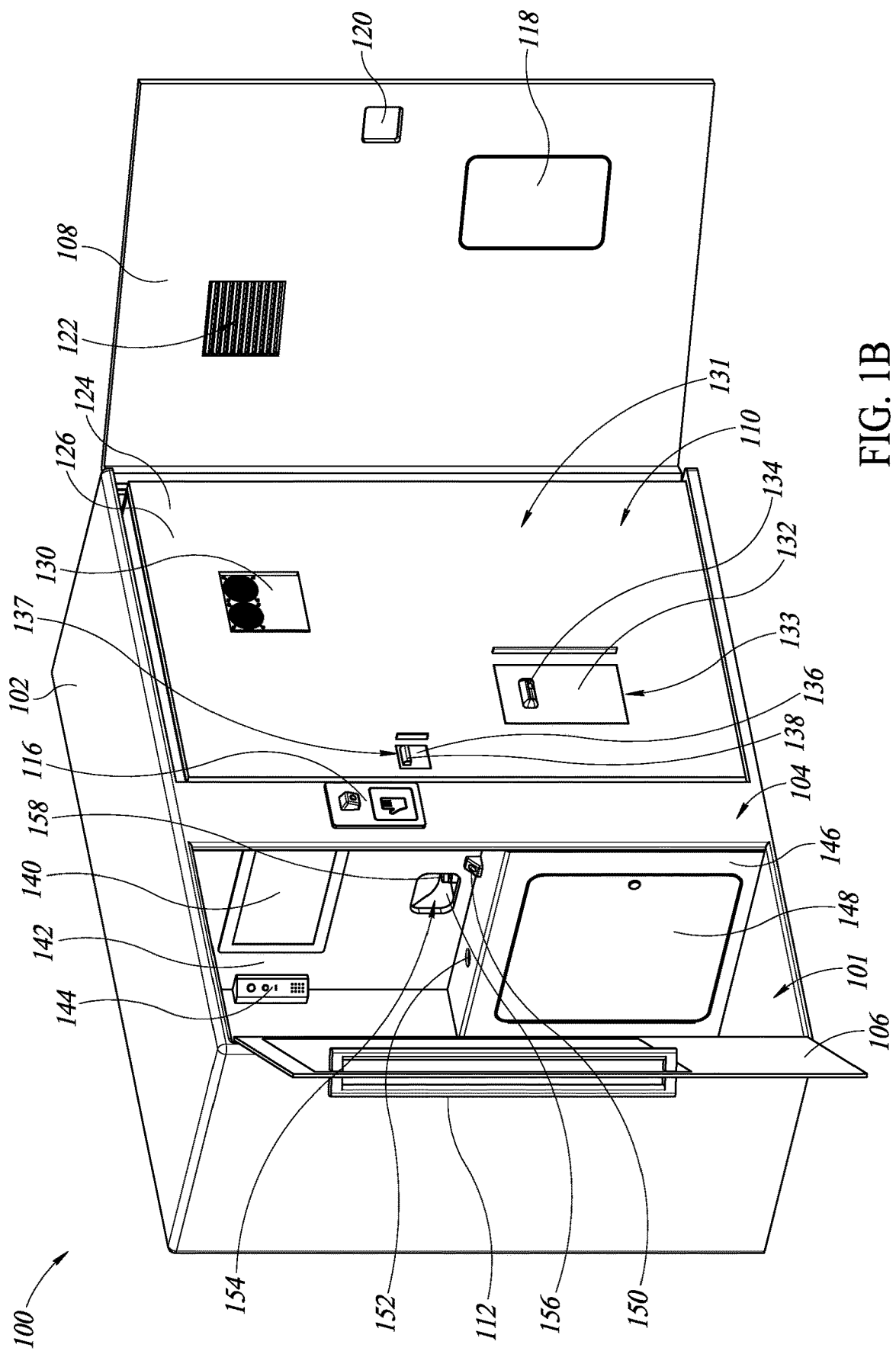
FIG. 1B is a perspective view of the embodiment of the kiosk as shown in FIG. 1A having doors that are coupled to the chassis in their opened positions.

FIG. 1B is a perspective view illustrating the embodiment of the kiosk 100 as shown in FIG. 1A having both the first and second doors 106, 108 in their respective opened positions, which have been rotated from their closed positions to their opened positions.

A safe 124 is housed within the medication compartment 110 of the chassis 102. The second door 108 limits access to the safe 124 when locked by the first lock (not shown or readily visible) in the closed position in which the second door 108 covers the safe 124. The safe generally is a safe lined with an insulating material to assist in maintaining or regulating a temperature within the safe 124 in which the mediation is stored to secure the medication from misappropriation (e.g., theft by breaking into the kiosk 100).

The safe 124 includes a third door 126 that limits access to an internal chamber 128 within the safe 124. The internal chamber 128 may be readily seen in FIG. 1C in which the third door 126 is in an opened position. The medication is stored within the internal chamber 128 of the safe 124.

A second lock, which is not shown or readily visible, may be in mechanical cooperation with the third door 126 to lock the third door 126 in a closed position to limit access to the internal chamber 128 within the safe 124. The second lock may be in electrical communication with the first biometric scanner 116. For example, if the first biometric scanner 116 is a finger print scanner, a maintenance employee may scan their finger print with the first biometric scanner 116, and, if the maintenance employee has proper approval, permission, or certification to open the third door 126, the second lock is unlocked such that the second door 108 may be opened to access the internal chamber 128 of the safe 124. The approval may be processed via interaction with the remote server or may be processed and stored in the stand-alone kiosk. For example, the first biometric scanner 116 is in electrical communication with a memory within the kiosk 100 that stores encrypted secure identifiable information such that when the maintenance employee scans their finger print with the first biometric scanner 116 the second lock is unlocked such that the maintenance employee may open the third door 126. Alternatively, this encrypted secure identifiable information may be stored remotely in a cloud in electrical communication (e.g., wired, wireless, or some combination of both wired and wireless electrical connections) with the first biometric scanner 116. The kiosk 100 will be configured to only unlock the second lock to the authorized maintenance employee after secure identification of the authorized maintenance employee has been confirmed. The cloud may be external to the kiosk 100. In some embodiments, the second lock may be replaced by a magnet closure system 129a, 129b, which may readily be seen in FIGS. 1C and 1D. The magnet closure system 129 may include first and second magnetic components 129a, 129b that hold the third door 126 in the closed position. However, when a user applies enough force to the third door 126 in attempting to open the third door 126 that is greater than the magnetic attraction force between the first and second magnetic components 129a, 129b, the third door 126 is opened.

The temperature adjustment module 130 is exposed from an outer surface 131 the third door 126 and is aligned with the plurality of vents 122 when the third door 126 is in the closed position. The temperature adjustment module 130 may be able to increase and decrease the temperature within the safe 124 to maintain or regulate the temperature within the internal chamber 128 at a selected temperature. For example, if the temperature is above a selected temperature, the temperature adjustment module 130 may decrease the temperature within the internal chamber 128 to be substantially at the selected temperature. Alternatively, if the temperature is below a selected temperature, the temperature adjustment module 130 may increase the temperature within the internal chamber 128 to be substantially at the selected temperature. The temperature adjustment within the internal chamber 128 utilizing the temperature adjustment module 130 provides proper storage of the medication within the internal chamber 128 to avoid expiration or deterioration of the medication before an expiration date of the medication, and may provide the capability to track the medication at a selected temperature with a thermal image camera to confirm ingestion of the medication to avoid diversion of the medication by a patient. The temperature adjustment module 130 may be a heating and cooling fan or some other module for regulating and maintaining the temperature within the internal chamber 128 of the safe 124.

A first drawer 132 is exposed from the outer surface 131 of the third door 126 and is in a first opening 133 in the third door 126. The first drawer 132 includes a first pull handle 134 exposed from the third door 126. The first drawer 132 extends through the first opening 133 in the third door 126 into the internal chamber 128 of the safe 124. The first drawer 132 may be a restock drawer utilized to restock a medication stored within the internal chamber 128 within the safe 124. The first drawer 132 may be removed from the internal chamber 128 by pulling on the first pull handle 134 of the first drawer 132. For example, a user, which may be an employee who is restocking the medication to be stored within the internal chamber 128, may pull on the first pull handle 134 of the first drawer 132 to remove the first drawer 134 from the safe without having to open the third door 126 of the safe 124. The user may then place medication within the first drawer 132 and then reinsert the first drawer 132 into the safe 124 through the first opening 133 in the third door 126. The first drawer 132 may be removed and inserted by sliding the first drawer 132 into and out of the first opening 133.

It is envisioned that the first drawer 132 may be restocked without opening the third door 126 to the safe 124. The first drawer 132 may be restocked through the second door 108 when in a closed position.

A second drawer 136 is exposed from the outer surface 131 of the third door 126 and is in a second opening 137 in the third door 126. The second drawer 136 includes a second pull handle, button, or latch (physical or electronic) 138 exposed from the third door 126. The second drawer 136 extends through the second opening 137 in the third door 126 into the internal chamber 128 of the safe 124. The second drawer 136 may be a restock drawer utilized to restock the medication stored within the internal chamber 128 within the safe 124. The second drawer 136 may be removed from the internal chamber 128 by pulling on the second pull handle 138 of the second drawer 136. For example, a user, which may be an employee who is restocking a medication to be stored in the internal chamber 128, may pull on second pull handle 138 of the second drawer 136 to remove the second drawer 136 from the safe without having to open the third door 126 of the safe 124. The user may then place medication within the second drawer 136 and then reinsert the second drawer 136 into the safe through the second opening 137 in the third door 126. The second drawer 136 may be removed and inserted by sliding the second drawer 136 into and out of the second opening 137.

By removing the first and second drawers 132, 136 without opening the third door 126, the temperature within the internal chamber 128 may be more readily maintained and regulated by the temperature adjustment module 130 to avoid the medication already present within the internal chamber 128 being exposed to an external environment. This reduces the likelihood the medication already present within the internal chamber 128 being exposed to the external environment outside the safe 124, which could increase the speed at which the medication already present within the internal chamber 128 deteriorates or expires.

The medication restocked utilizing the second drawer 136 may be a different type of medication as compared to the medication restocked utilizing the first drawer 134. Alternatively, the medication restocked utilizing the second drawer 136 may be the same as the medication restocked utilizing the first drawer 134. However, while the medication may be the same, the medication may be in different forms. For example, the medication restocked utilizing the second drawer 136 may be in strips 200 (see FIG. 1F) of medication that dissolve when placed on a tongue of a patient for ingestion by the patient. These strips can be packaged in individual wrappers, which are often in a thin, flat configuration, like a credit card. The medication restocked utilizing the first drawer 132 may be in pill or liquid form stored in bottles that are ingested by the patient by being swallowed.

A third lock (not shown or readily visible) may lock the first hatch 118 to limit access to the first drawer 132 when the first hatch 118 is closed, and a fourth lock (not shown or readily visible) may lock the second hatch 120 to limit access to the second drawer 136 when in the second hatch 120 is closed. The third and fourth locks may be in electrical communication with the first biometric scanner 116 such that when the first biometric scanner 116 identifies a user with certification, approval, or permission to access the first drawer 132 and/or the second drawer 136, the third lock, the fourth lock, or both may be unlocked such that the first hatch 118 and/or second hatch 120 are capable of being opened. This provides the user access the first drawer 132 and/or the second drawer 136 through the first and second hatches 118, 120, respectively. In other words, when the third lock is locked, the first drawer 132 may not be removed as the first hatch 118 limits access to the first drawer 132, and, when the fourth lock is locked, the second drawer 136 may not be removed as the second hatch 120 limits access to the second drawer 136.

A video conference display 140 is within the patient compartment 101 and on a wall 142 that separates the patient compartment 101 from the medication compartment 110. The wall 142 partially delimits the patient compartment 101. The video conference display 140 may be a liquid crystal display (LCD), a digital display, a smart tablet, or some other type of video conference display. The video conference display 140 may include a camera, a speaker, a touch screen, and a microphone such that a medical professional may monitor and interact with a patient within the patient compartment when the medication is being dispensed to the patient. For example, the medical professional may confirm a patient's identity by looking at the patient through the video conference display 140, may monitor and observe the patient's ingestion of a dispensed medication to reduce the likelihood of diversion or misappropriation of the medication for other unintended purposes, and may have discussions with the patient for providing additional medical assistance or recommendations based on their professional opinion.

A first audio component 144 is present at a first corner of the patient compartment 101. The first audio component 144 may include a speaker, a microphone or some other type of audio component. For example, the first audio component 144 may be in electrical communication with the video conference display 140 such that the first audio component 144 allows for a patient to talk to a medical professional through the first audio component 144.

A shelf 146 is within the patient compartment 101. The shelf 146 is a hollow shelf and includes a fourth door 148 that provides access to a compartment 149 behind the fourth door 148. The compartment 149 may readily be seen in FIG. 1I and the details of which will be discussed with respect to FIG. 1I.

A second biometric scanner 150 is on the shelf 146 and is within the patient compartment 101. The second biometric scanner 150 is accessible to a patient when in the patient compartment. Similar to the first biometric scanner 116, the second biometric scanner 150 may be a finger or hand print scanner, a facial identification scanner, a retinal scanner, or some other type of biometric scanner or some other combination of biometric scanners. Alternatively, if the second biometric scanner 150 is a combination of different types of biometric scanners, the second biometric scanner 150 may be a retinal and facial identification scanner, may be a finger print and retinal scanner, or may be some other combination of types of biometric scanners.

A fifth lock (not shown or readily visible) is in mechanical cooperation with the fourth door 148 and locks the fourth door 148 when in the closed position as shown in FIG. 1B. The fifth lock may be in electrical communication with the second biometric scanner 150 such that the fifth lock may be unlocked when the second biometric scanner 150 identifies a user such as a maintenance employee with approval, certification, or permission to access the fourth door 148. For example, the second biometric scanner 150 is in electrical communication with a memory within the kiosk 100 that stores encrypted secure identifiable information such that when the maintenance employee scans their finger print with the second biometric scanner 150 the fifth lock is unlocked such that the maintenance employee may open the third door 126. Alternatively, this encrypted secure identifiable information may be stored remotely in a cloud in electrical communication (e.g., wired or wireless) with the first biometric scanner. The kiosk 100 will be configured to only unlock the second lock to the authorized maintenance employee after secure identification of the maintenance employee has been confirmed. The cloud may be external to the kiosk 100.

A one-way receptacle 152, which may be a one-way valve, extends through the shelf and limits access to the compartment 149 in a first direction directed from within the patient compartment 101 into the compartment 149 within the shelf 146. The one-way receptacle 152 is configured to receive an empty medication container that previously contained medication ingested by a patient, and, after the medication is ingested by the patient, the patient places the empty medication container into the compartment 149 through the one-way receptacle 152. The disposal of the empty medication container avoids misappropriation of the patient's confidential information (e.g., identity theft) as the empty medication container may include labels or information confidential to the patient.

A dispense opening 154 extends through the wall 142 and is accessible from within the patient compartment 101. The dispense opening 154 is in fluid communication with a dispense structure 156. The dispense opening 154 may be referred to as a medication dispense opening through which a patient may access a medication provided through or dispensed through the dispense structure 156.

The dispense structure 156 may be a hollow structure that extends from within the medication compartment 110 to within the patient compartment 101 such that a medication container 158 may be dispensed through the dispense structure 156 such that a patient may obtain the medication container 158 through the dispense opening 154. The medication container 158 may be one of a plurality of medication containers 158 that may be stored within the medication compartment 110. As discussed earlier, the patient may then ingest the dosage of medication within the medication container 158, and then dispose of the medication container 158 through the one-way receptacle after ingesting their medication.

The dispense structure 156 may be lined with a cushion material to reduce the likelihood of the medication container 158 breaking when being dispensed to a patient in the patient compartment 101. For example, the cushion material may be a foam material, a polyester fiberfill, a polyurethane foam, or some other type of material that will cushion the medication container 158 being dispensed through the dispense structure 156.

While not readily visible, a valve structure or insulation barrier may be present along and within the hollow structure of the dispense structure 156 between the first end and the second end of the dispense structure 156. The valve structure or insulation barrier prevents cold air within the internal chamber 128 of the safe 124 passing through the dispense structure 156 from the medication compartment 110 to the patient compartment 101 through the dispense structure 156. In other words, the valve structure or insulation barrier limits the transfer of cold air in the internal chamber 128 of the safe 124 to the patient compartment through the dispense structure 156. The valve structure or insulation barrier is structured such that the medication containers 158 containing doses of medication may readily pass by or through the valve structure or insulation barrier when being dispensed to an authorized patient utilizing the dispense structure 156.

The valve structure or the insulation barrier may be structured as a one-way structure or barrier such that a patient within the patient compartment 101 may not reach through the dispense structure 156 into the medication compartment 110. In other words, the valve structure or the insulation barrier may be a one-way structure that prevents the patient from accessing the medication compartment 110 through the dispense structure 156, which is accessible from the patient compartment 101. Alternatively, a one-way structure separate from the valve structure or the insulation barrier may be present within the dispense structure 156 to prevent the patient from accessing the medication compartment 110 through the dispense structure 156, which is accessible from the patient compartment 101. For example, the one-way structure may be the same or similar to a one-way structure of a vending machine such that a user of the vending machine may not steal products present within the vending machine.

The medication container 158 may be a bottle, a vial, or some other type of medication container. The medication container 158 may be plastic, glass, metallic, or some other suitable material for a medication container. The medication container 158 may include a cap that locks when in a closed position. The medication container 158 may contain a dose of methadone, a dose of buprenorphine, or some other type of medication (e.g., pharmaceutical agent) to be dispensed to a patient.

Figure 1C:
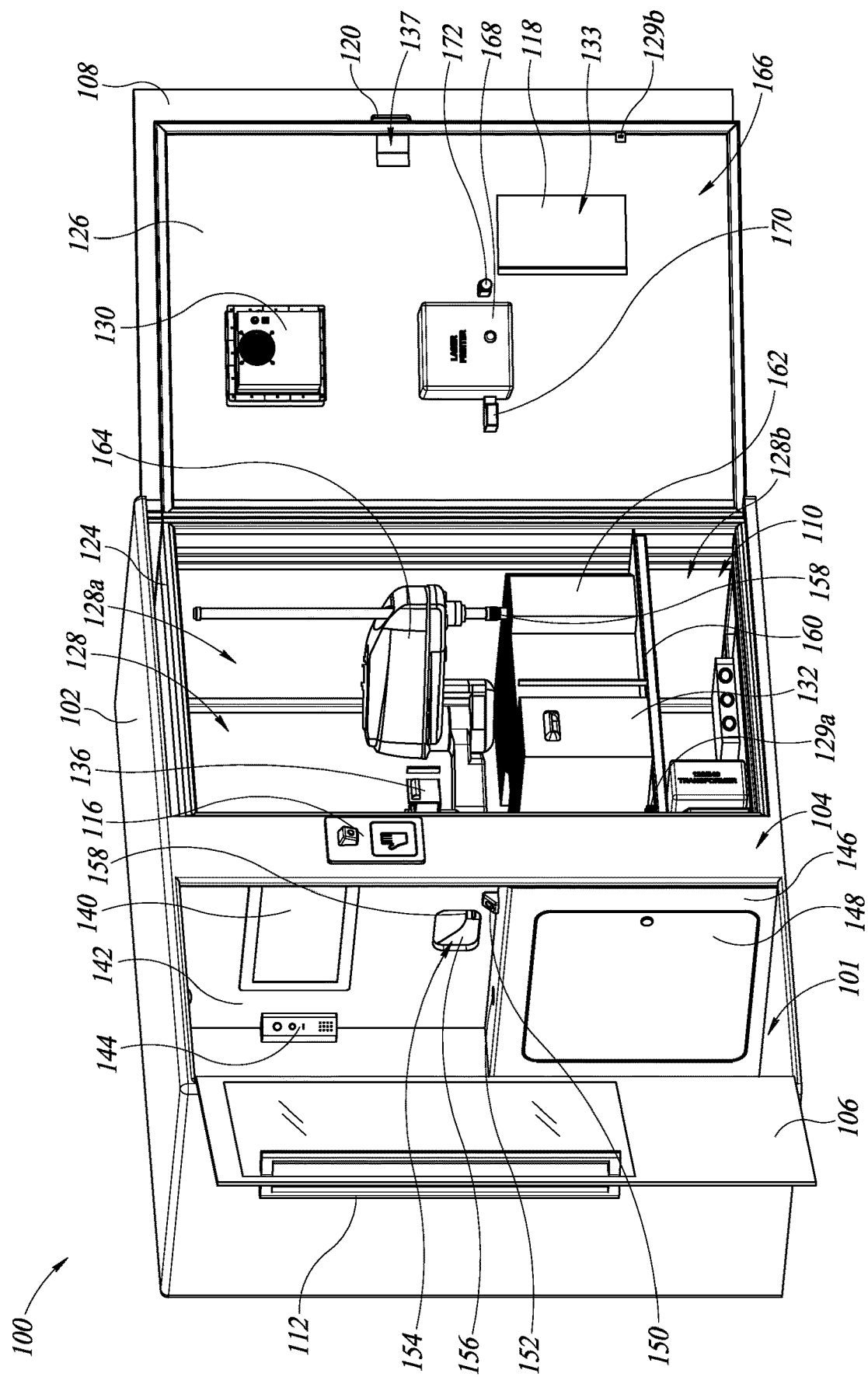
FIG. 1C is a perspective view of the embodiment of the kiosk as shown in FIGS. 1A and 1B having the doors that are coupled to the chassis in their opened positions and a door of the safe in an opened position.

FIG. 1C is a perspective view of the embodiment of the kiosk 100 as shown in FIGS. 1A and 1B having the first and second doors 106, 108 that are coupled to the chassis 102 in their opened positions, respectively. Unlike FIG. 1B, as shown in FIG. 1C, the third door 126 of the safe 124 is in the opened position as well.

The internal chamber 128 includes a first portion 128a and a second portion 128b that are separated from each other by a divider 160. The first portion 128a contains medication that is stored within the internal chamber 128 of the safe 124, and the second portion 128b contains electronics to assist in the functionality of the kiosk 100. The first portion 128a and the second portion 128b may be insulated from each other such that the temperature within the first portion 128a of the internal chamber 128 is different from the temperature in the second portion 128b. For example, the divider 160 may include an insulting material that insulates the first portion 128a from the second portion 128b and vice versa. The second portion 128b may be closer to the top or ceiling of the safe 124 in an alternative design.

A medication container storage case, container, or structure 162 is within the first portion 128a of the internal chamber 128, and the storage case 162 is on the divider 160 that extends across the internal chamber 128. The divider may be a shelf, a platform, or some other structure for separating and dividing the internal chamber into the first portion 128a and the second portion 128b. The storage case 162 is adjacent to the first drawer 132, which is on the divider 160.

A manipulator 164 is within the first portion 128a of the internal chamber 128. In this embodiment of the kiosk 100, the manipulator 164 is a pneumatic robotic arm that transfers respective medication containers 158 stored within the storage case 162 to the dispense structure 156. The manipulator 164 may be a Fanuc Scara robotic arm. The manipulator 164 may have multiple axes (e.g., Cartesian axes and rotation axes) of movement. For example, in some embodiments, the manipulator 164 may have 4-axes about which the manipulator may articulate, actuate, and move.

An end effector of the manipulator 164 may pick up a respective medication container 158 stored in the storage case 162 and deposit the respective medication container 158 into the dispense structure 156 such that the respective medication container 158 containing the medication for a patient may be obtained by the patient through the dispense opening 154. For example, the manipulator 164 may pick up the respective medicine container 158 from within the storage case 162 utilizing an end effector (e.g., gripper, jaw, clamp, or some other suitable type of end effector) of the manipulator 164 that grips a cap of the medicine container 158, moves the respective medication container 158 to the dispense structure 156, and then drops the medicine container 158 into the dispense structure 156 such that a patient within the patient compartment 101 may obtain the respective medication container 158 through the dispense opening 154.

The third door 126 of the safe 124 includes an inner surface 166 opposite to the outer surface 131. The temperature adjustment module 130 is present at the inner surface 166 of the third door 126 such that the temperature adjustment module 130 rotates with the third door 126 when the third door 126 is opened as shown in FIG. 1C.

A printer 168 is on the inner surface 166 of the third door 126. The printer 168 may be a laser printer. The printer 168 may print labels that may be applied to a respective medication container 158 before being placed in the dispense structure 156 by the manipulator 164. For example, the manipulator 164 may pick up the respective medication container 158 stored within the storage case 162, and move the respective medication container 158 to the printer 168 such that a label printed from the printer 168 may be applied to the respective medication container 158. The label may be applied to the respective medication container 158 by utilizing the manipulator 164 to press the respective medication container 158 against an adhesive on the label. After being pressed against the adhesive, the manipulator 164 may rotate to facilitate adhesion of the label to the respective medication container 158. The label may include personal identification information for the patient obtaining their medication utilizing the kiosk 100. The printer may be on a interior wall of the safe 124 instead of the door.

A first scanner 170 is present at the inner surface 166 of the third door 126 of the safe 124. The first scanner 170 may be a barcode scanner, a radio frequency identification (RFID) scanner, or some other type of scanner. The first scanner 170 may scan a barcode, an RFID tag, a quick response (QR) code, or some other type of identification feature on a respective medication container 158 when dispensing the respective medication container 158 to a patient obtaining their medication. For example, the manipulator 164 may pick up the respective medication container 158 and bring a barcode or an RFID tag on the respective medication container 158 within the field of view (FOV) or scanning area of the scanner such that the barcode or RFID tag may be scanned for record keeping purposes. This scanned information may be kept for record keeping purposes to later reference as to whether the proper medication was provided to a patient, or this scanning may be an additional confirmation step before providing the respective medication container to the patient. The barcode or the RFID tag may already be on the respective medication container 158 before the respective medication container was placed within the storage case 162.

A first camera 172 is present at the inner surface 166 of the third door 126 of the safe 124. The first camera 172 may take an image of a label (e.g., serial number, QR code, or some other identification feature) on the respective medication container 158 before providing the medication container 158 to a patient for record keeping purposes or real-time confirmation from a medical professional that is remote from the patient. The first camera 172 may take an image of the medication container 158 for record keeping purposes. For example, the manipulator 164 may pick up the respective medication container 158 and bring the respective medication container 158 within the FOV of the first camera 172 at which point the first camera 172 captures an image of the label on the respective medication container 158. The label may already be applied to the respective medication container before being placed within the storage case 162, or the label may be a label that has been printed by the printer 168 and applied to the respective medication container 158 in the manner as discussed earlier in the present disclosure.

Figure 1D:
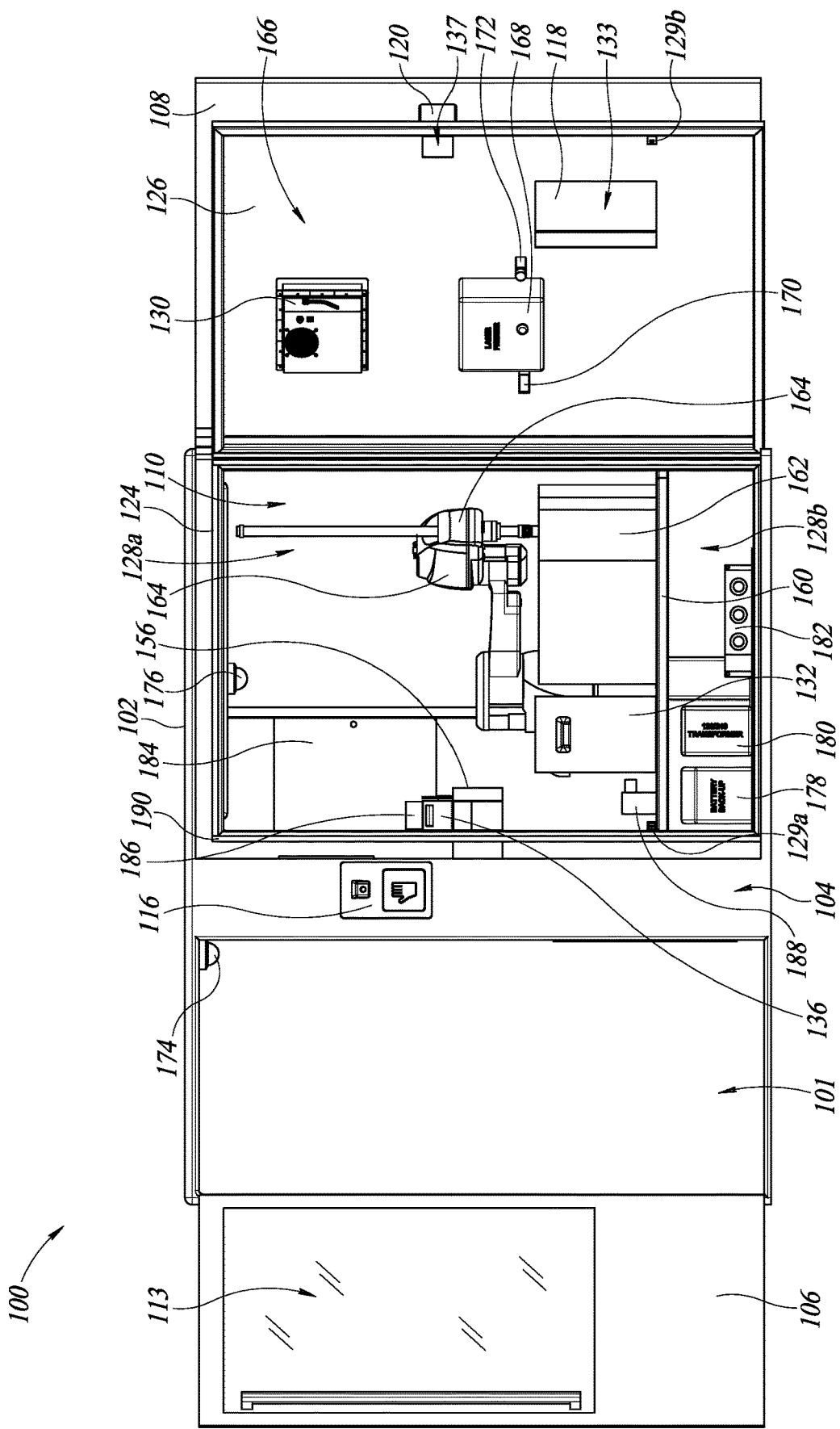
FIG. 1D is a front side view of the embodiment of the kiosk as shown in FIGS. 1A and 1B having the doors that are coupled to the chassis and the door of the safe in their opened positions.
Figure 1E:
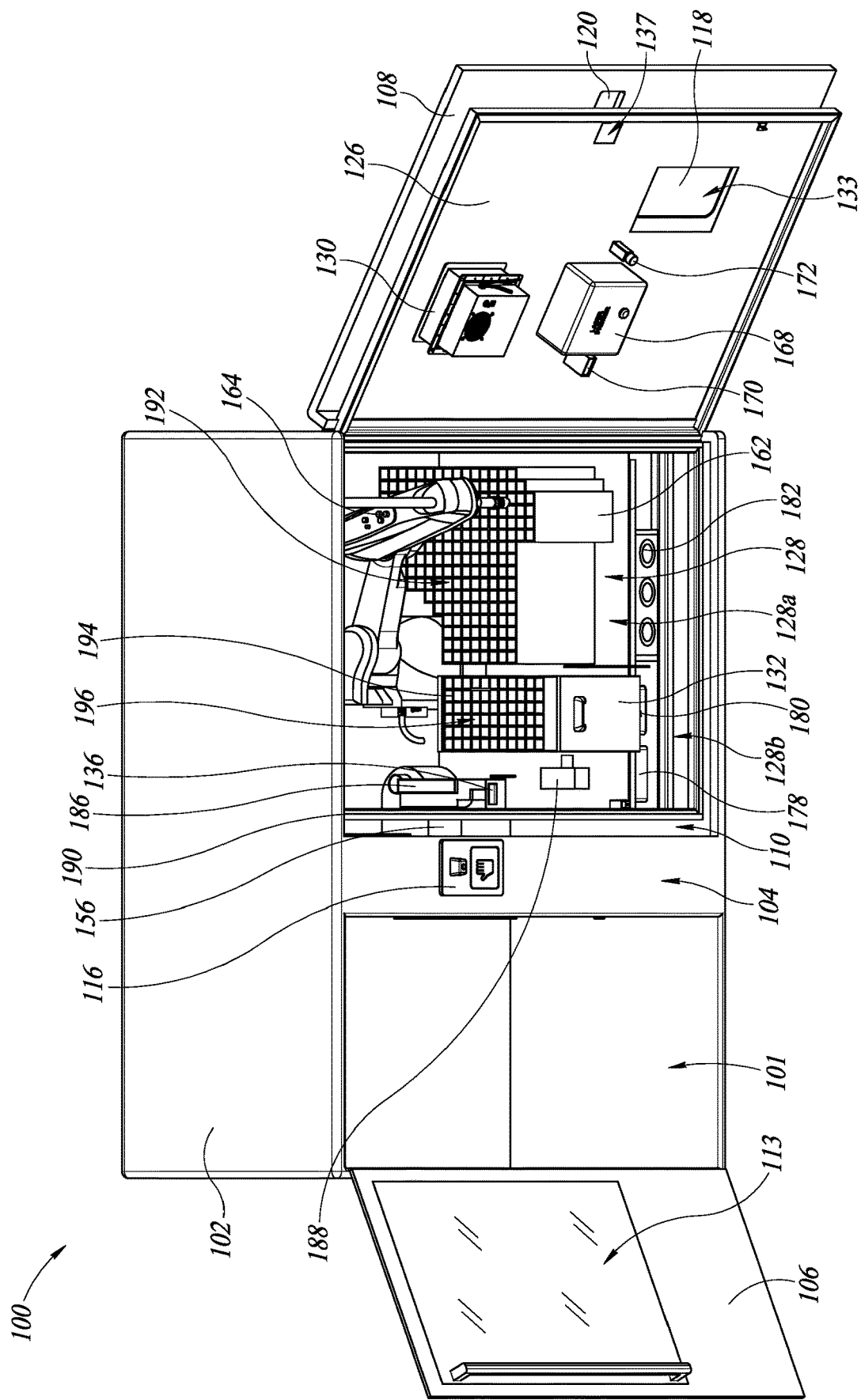
FIG. 1E is a front side elevated view of the embodiment of the kiosk as shown in FIGS. 1A and 1B having the doors that are coupled to the chassis and the door of the safe in their opened positions.

FIG. 1D is a front side view of the embodiment of the kiosk 100 as shown in FIGS. 1A and 1B. FIG. 1E is a front side elevated view of the embodiment of the kiosk 100 as shown in FIGS. 1A and 1B. In FIGS. 1D and 1E, the first, second, and third doors 106, 108, 126, respectively, are in their opened positions A first surveillance camera 174 is on a ceiling of the patient compartment 101, and a second surveillance camera 176 is in the internal chamber 128 of the safe 124 and is on a ceiling of the safe 124. The first and second surveillance cameras 174, 176, respectively, monitor the patient compartment 101 and the internal chamber 128 of the safe 124, respectively. For example, the first and second surveillance cameras 174, 176 may monitor the patient compartment 101 and the internal chamber 128 twenty-four hours a day, seven days a week (24/7). In other words, the first and second surveillance cameras 174, 176 are always on and are always monitoring the patient compartment 101 and the internal chamber 128, respectively. In an alternative situation, the first and second surveillance cameras 174, 176 may be coupled to motion detectors that send an electrical signal to turn on the first or second surveillance camera 174, 176 when a motion is detected. The first and second surveillance cameras 174, 176 may be fisheye lensed surveillance cameras, panoramic cameras, or some other type of surveillance camera that readily monitors the entirety of the patient compartment 101 and the internal chamber 128, respectively.

The first surveillance camera 174 monitors the patient compartment 101 and records a patient when the patient is within the patient compartment 101. For example, the first surveillance camera 174 records the patient's actions while the patient is interacting with a medical professional through the video conference display 140 such as when the patient ingests their medication.

The second surveillance camera 176 monitors the internal chamber 128 and records an employee or individual accessing the internal chamber 128. For example, when a maintenance employee is accessing the internal chamber 128 to perform routine maintenance on the manipulator 164, the second surveillance camera 176 records the maintenance employee to reduce the likelihood of medication within the internal chamber 128 being removed by the maintenance employee. Alternatively, when an employee is restocking the internal chamber 128 with medication, the second surveillance camera 176 records the internal chamber 128 during the restock process to reduce the likelihood of medication within the internal chamber being removed by the employee.

While not shown, in an alternative embodiment, a third surveillance camera may be present at the external surface 104 of the chassis 102 to monitor and record individuals accessing either the patient compartment 101 or the medication compartment 110 of the chassis 100. In some embodiments, the third surveillance camera may be on twenty-four hours, seven days a week (24/7). In some other embodiments, the third surveillance camera may turn on when a motion detector detects a motion at a selected distance from the kiosk 100 (e.g., an individual approaching the kiosk 100). The third surveillance camera may be present in some embodiments to reduce the likelihood of attempts of theft or misappropriation of medication stored within the kiosk 100. In yet some other alternative embodiments, there may be additional cameras within the kiosk 100 or along the external surface 104 of the kiosk 100 to monitor the kiosk 100 and reduce the likelihood of theft or misappropriation of medication stored within the kiosk 100.

While not shown, in an alternative embodiment, an alarm system may be in the kiosk 100 such that if an individual tries to break into the kiosk 100, the alarm system will go off to alert security that an unapproved, unpermitted, or uncertified access (e.g., theft or break-in) has occurred. The alarm system may be an audio alarm, a visual alarm, or some other type of alarm.

A battery 178 is within the second portion 128b of the internal chamber 128. The battery 178 may be a backup battery electrically coupled to electrical components of the kiosk 100 such that the kiosk 100 still functions when there is a power outage. For example, the battery 178 may be electrically coupled to the temperature adjustment module 130, the first and second surveillance cameras 174, 176, electro-mechanical locks that limit access to the kiosk 100 (e.g., lock the second door 108, the third door 126, the first hatch 118, the second hatch 120, or some other door, hatches, or access points of the kiosk 100), and the manipulator 164. The battery 178 may be coupled to other electronic components of the kiosk 100 as well to supply power in the event of a power outage.

For example, if a power outage were to occur, the battery 178 supplies power to the temperature adjustment module 130 to maintain and regulate the temperature within the internal chamber 128 such that medication stored within the internal chamber does not deteriorate and expire. Similarly, the battery 178 supplies power to the electro-mechanical locks and the respective surveillance cameras 174, 176 such that unapproved, unpermitted, or uncertified individuals are deterred and limited from accessing medication stored within the internal chamber 128 of the safe 124. In some instances, the battery 178 may supply power too all of the electronic components within the kiosk 100 such that the kiosk 100 continues to fully operate such that a patient may obtain their medication utilizing the kiosk 100 even in the event of a power outage.

However, electrical circuitry within the kiosk may prioritize supplying power to certain electrical components over other electrical components utilizing the battery 178 in the event of a power outage. For example, if the battery 178 has a power level below a selected power level threshold, the electrical circuitry may limit the battery 178 to only supplying power to the temperature adjustment module 130, the electro-mechanical locks, and the first and second surveillance cameras 174, 176 to reduce the likelihood of deterioration or expiration of the medication and reduce the likelihood of misappropriation (e.g., theft) of the medication in the kiosk 100.

A transformer 180 is within the second portion 128b of the internal chamber 128. The transformer 180 is electrically coupled to the electrical components of the kiosk 100 such that the transformer steps-up or steps-down a voltage of an electrical signal provided by a power source external to the kiosk 100 or provided by the battery 178. For example, the transformer 180 may be electrically coupled to the temperature adjustment module 130, the first and second surveillance cameras 174, 176, electro-mechanical locks that lock access to the kiosk 100 (e.g., lock the second door 108, the third door 126, the first hatch 118, the second hatch 120, or some other door, hatches, or access points of the kiosk 100), and the manipulator 164.

A fan 182 is within the second portion 128b of the internal chamber 128. The fan 182 may assist in regulating the temperature of the second portion 128b of the internal chamber 128. The fan 182 may be a heating fan, a cooling fan, or both such that the fan 182 may readily adjust a temperature within the second portion 128b of the internal chamber 128 to reduce the likelihood of the battery 178 and the transformer 180 overheating or to reduce the likelihood the battery 178 and the transformer 180 falling below a selected temperature.

A control box 184 is within the first portion 128a of the internal chamber 128 of the safe 124. The control box 184 contains additional electrical circuitry and components such that the kiosk 100 functions. For example, the control box 184 may contain a memory that is in electrical communication with the manipulator 164. The memory may contain control instructions that are sent as control signals to the manipulator 164 to dispense the medication containers 158 within the internal chamber 128 through the dispense structure 156 utilizing the manipulator 164. Alternatively, the memory may contain control instructions that are sent as control signals to move or reorganize medication containers 158 within the internal chamber 128 utilizing the manipulator 164.

The control box 184 may further or alternatively contain a central processing unit (CPU) and a transceiver that is in electrical communication (e.g., wired, wireless, or some combination of both wired and wireless connections) with the CPU. The transceiver is in electrical communication (e.g., wired, wireless, or some combination of both wired and wireless connections) with a cloud external to the kiosk 100. The CPU is configured to send and receive electrical signals to and from the cloud through the transceiver. In other words, the CPU within the control box 184 may receive input signals from the cloud through the transceiver, and the CPU within the control box 184 may send output signals to the cloud through the transceiver.

For example, the CPU may be in electrical communication with the first and second biometric scanners 116, 150 such that when a user scans their biometric information (e.g., fingerprint, retina, face, etc.) utilizing the first or second biometric scanner 116, 150 their biometric information is processed by the CPU and is transmitted to the cloud through the transceiver. The biometric information transmitted to the cloud may then be compared to encrypted secure identifiable information (e.g., biometric data) stored in the cloud to determine whether the user has authorization to access the kiosk 100.

The secured encrypted identifiable information (e.g., biometric data) stored on the cloud may have been previously obtained from and provided by a patient. For example, the patient provides the biometric information at a doctor's office, a clinic for addiction treatment, a pharmacy, or other biometric information collection location. This biometric information is collected and stored in a database on the cloud that is accessible by an entity managing the kiosk 100 or a distribution network of a plurality of the kiosks 100. This database is configured to communicate the biometric data to each individual device through a wired communication mechanism or remotely through wireless transmission means, such as WiFi, Bluetooth, or cellular networks. The kiosk 100 will include a plurality of communication devices, such as through the data port in a wired configuration, or a wireless transceiver housed within the kiosk 100 to communicate with the cloud and the database on the cloud.

In at least one situation, if the comparison results in a positive identification of an authorized maintenance employee, a signal may be sent from the cloud to through the transceiver to the CPU. Upon receipt of the signal, the CPU may process the signal and send a control signal to a respective lock unlocking the lock and providing the maintenance employee access to selected regions/areas of the kiosk 100.

Alternatively, in at least one other situation, if the comparison results in a positive identification of an authorized patient, a signal may be sent from the cloud through the transceiver to the CPU. Upon receipt of the signal, the CPU may process the signal and send a control signal to the manipulator 164 such that the manipulator picks up a medication container 164 to eventually be released into the dispense structure 156 such that the authorized patient may then obtain their medication for ingestion.

The control box 184 may be regulated in temperature such that the electronic circuitry and components within the control box 184 do not overheat or fall below a selected temperature. For example, a temperature adjustment module may be present within the control box 184 to regulate a temperature within the control box 184 to reduce the likelihood of overheating of electrical components (e.g., CPU, transceiver, motherboard, electrical circuitry, etc.) within the control box 184. The temperature adjustment module within the control box 184 may be an air conditioning system, a fan, or some other type of temperature adjustment module to regulate the temperature within the control box 184.

An actuator 186 is within the first portion 128a of the internal chamber 128 of the safe 124. The actuator 186 may be a linear actuator that includes an end effector (e.g., a gripper, a suction gripper, jaw gripper, a clamp gripper, or some other type of end effector) that picks up a package 200 containing a strip of medication (see FIG. 1F) in the second drawer 136, moves the package 200 to the dispense structure 156, and deposits (e.g., drops) the strip 200 of medication for ingestion by a patient within the patient compartment 101. The package 200 of strip of medication may be within a package such as a wrapper that is opened by the patient before ingesting the package 200 of strip of medication. The strip of medication may be ingested by a patient such that when the patient places the strip of medication onto their tongue to dissolve.

A second scanner 188 is within the first portion 128a of the internal chamber 128 of the safe 124. The second scanner 188 may be a barcode scanner, RFID scanner, or some other identification scanner. The details of the second scanner will be discussed further with respect to FIG. 1G as follows within the present disclosure.

The dispense structure 156 as shown in FIG. 1E extends through a first sidewall 190 of the safe 124 into the first portion 128a of the internal chamber 128 such that the dispense structure 156 extends from the patient compartment 101 to the first portion 128a of the internal chamber 128. As discussed earlier, the manipulator 164 deposits a respective medication container 158 into the dispense structure 156 to provide medication to a patient within the patient compartment 101.

The storage case 162 as shown in FIG. 1E has an irregular polygonal shape or irregular polygonal prism shape when viewed in the front side elevated view as shown in FIG. 1E. The irregular shape of the storage case 162 allows for the storage case 162 to maximize or optimize utilization of space within the internal chamber 128 such that the storage case 162 has the largest possible capacity for storing medication containers containing various dosages of medication. For example, the medication containers 158 stored in the storage case 162 may have differing amounts of dosages of a medication, which may be methadone for treating opioid addictions. For example, there may be forty different dosage amounts that are contained in any number of the plurality of medication containers. These dosage amounts may be 5-milligrams (mg), 10-mg, 15-mg, or any dosage amount that increases in increments of 5-mg up to a 100-mg dosage of medication. These dosage amounts may be 100-mg, 110-mg, 120-mg, or any dosage amount that increase in increments of 10-mg up to 300-mg.

Alternatively, these dosage amounts of medication within the plurality of medication containers 158 may be different for each and every medication container of the plurality of medication containers 158 stored within the storage case 162. For example, the dosage amount of each medication container 158 of the plurality of medication containers 158 may contain a customized dosage for each specific individual patient that has permission and access to utilize the kiosk 100. In other words, the dosage amount in each medication container 158 of the plurality of medication containers 158 may be any dosage amount.

First respective ones of the medication containers 158 may container a first type of medication, and second respective ones of the medication container 158 may container a second type of medication different from the first type of medication. For example, the first respective ones of the medication containers 158 may contain a dose of methadone whereas the second respective ones of the medication containers 158 may contain a dose of buprenorphine. In other words, ones of the medication containers 158 may contain different types of medications to treat different ailments. For example, methadone may be utilized to treat an opioid addiction of a patient participating in an OTP, and a dose of buprenorphine may be utilized in treating pain of the patient suffering from an opioid addiction to treat the opioid addiction of the patient participating in the OTP. This different medication in ones of the medication containers 158 may allow for the kiosk 100 to dispense different types of medication to the patient to treat multiple different types of ailments of the patient.

The storage case 162 includes a matrix or an array or a plurality of recesses 192. Each of the recesses 192 is sized and shaped to receive multiples of the plurality of medication containers 158. For example, a first recess of the matrix of recesses 192 may receive five of the medication containers 158 that are stacked on each other, a second recess of the matrix of recesses 192 may receive four of the medication containers 158, and a third recess of the matrix of recesses 192 may receive three of the medication containers 158 stacked on each other.

The second and third recesses may receive fewer of the medication containers 158 relative to the first recess as the medication containers 158 in the second and third recesses may be larger relative to the medication containers 158 in the first recess. For example, the medication containers 158 in the second and third recesses may be larger due to containing a larger dosage amount of medication relative to the medication containers 158 in the first recess.

Alternatively, the medication containers 158 in the first, second, and third recesses may all be relatively the same size and shape as each other. However, ones of the medications containers 158 in the second and third recesses may have been removed by the manipulator 164 and dispensed to patients through the patient compartment 101. Whereas no medication containers 158 may yet have been removed from the first recess to be dispensed to a patient in the patient compartment.

As readily shown in FIG. 1E, a medication restock container or insert 194 is inset within the first drawer 132. In other words, the medication restock container 194 is removably received by the first drawer 132 such that the medication restock container 194 may be lifted up to be removed from the first drawer. For example, the medication restock container 194 may be lifted up and out of the first drawer 132 while restocking the kiosk 100 with medication. The medication restock container 194 may be referred to as a medication refill container, a restock container, a refill container, or some other type of container that may be utilized to restock the kiosk with medication.

A matrix or an array of a plurality of recesses 196 are within the medication restock container or cartridge 194 similar to the matrix or array of the plurality of recesses 192 of the storage case 162. Similar to the recesses 192 of the storage case 162, the recesses 196 of the medication restock container 194 may contain new medication containers 158 to restock the storage case 162 in the internal chamber 128 with medication. For example, the medication containers 158 within the recesses 196 of the medication restock container 194 are removed from the recesses 196 of the medication restock container 194 by the manipulator 164 and then placed into the recesses 192 of the storage case 162 by the manipulator 164.

Figure 1F:
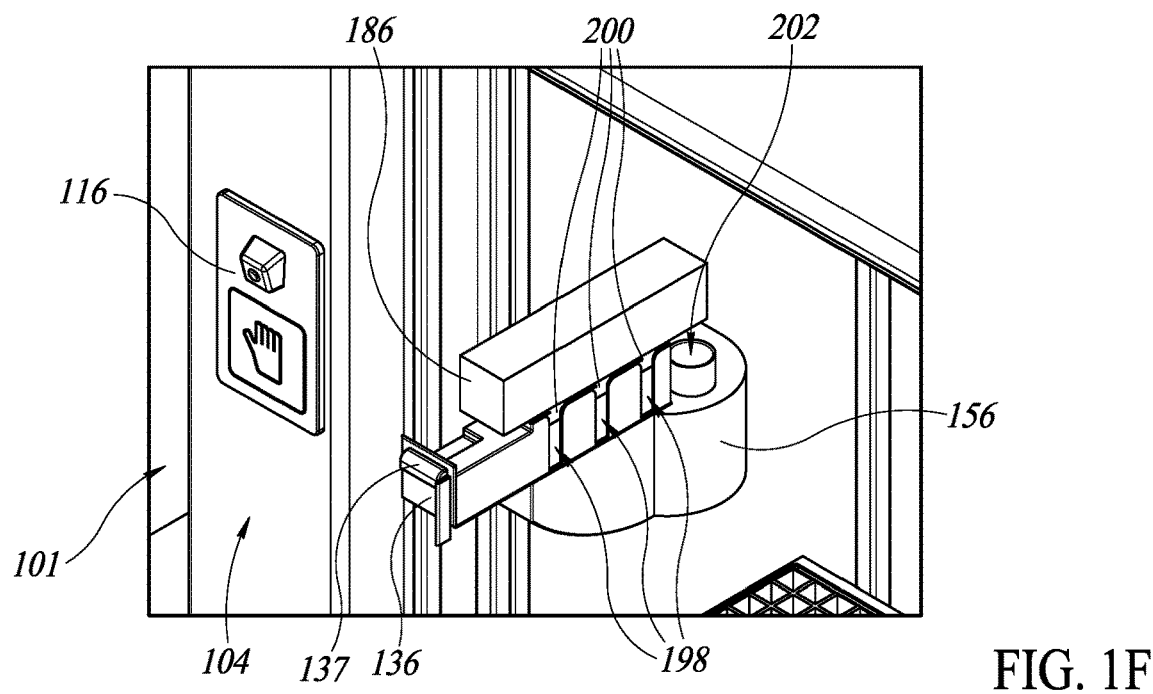
FIG. 1F is a zoomed in perspective view of a drawer of the safe that extends into the internal chamber of the safe when closed.

FIG. 1F is a zoomed in perspective view of the second drawer 136 and the actuator 186. The second drawer 136 includes a plurality of recesses 198 that receives packages 200 containing a strip of medication, which is a dissolvable and ingestible strip of medication (e.g., pharmaceutical agent). The strips of medication may be buprenorphine or some other type of treatment.

The dispense structure 156 includes a reception opening 202 in which the respective medication containers 158 or the packages 200 are deposited (e.g., dropped into or placed within). The reception opening 202 is in fluid communication with the dispense opening 154. When one of the medication containers 158 or one of the packages 200 is deposited into the reception opening 202, the respective medication container 158 or the respective package 200 travels along and through the dispense structure 156 such that a patient in the patient compartment 101 may receive the respective medication container 158 or the respective package 200 through the dispense opening 154. In this embodiment, the reception opening 202 has a cylindrical shape. However, in some embodiments, the reception opening 202 may have a rectangular shape, a square shape, or diamond shape, or some other shape sized to receive one of the respective medication container 158.

The actuator 186 is within the first portion 128*a* of the internal chamber 128 of the safe 124. As discussed earlier, the actuator 186 may be a linear actuator that includes a end effector (e.g., a gripper, suction gripper, jaw gripper, clamp gripper, or some other type of end effector).

In operation, the actuator 186 moves the end effector of the actuator 186 to be aligned with one of the recesses 198 that contains ones of the packages 200. Once the end effector is in place and aligned with one of the recesses 198, the end effector is lowered down and picks up a respective one of the packages 200. While holding the respective package 200, the end effector of the actuator 186 then raises up the end effector, and then the actuator 186 moves the end effector holding the respective package 200 to be aligned with the reception opening 202. Once the end effector is aligned with the reception opening 202, the end effector of the actuator 186 releases the respective package 200 to deposit (e.g., drop) the respective package 200 into the reception opening 202 of the dispense structure 156. The respective package 200 is then transported along the dispense structure 156 to an end of the dispense structure 156 that is accessible through the dispense opening 154 in the patient compartment 101. At this point, the patient may pick up and open the respective package 200 to access the strip of medication within the respective package 200, take the strip of medication out of the respective package 200, and then place the strip of medication onto their tongue to ingest the strip of medication (e.g., dissolves on tongue of patient).

The respective packages 200 in the left-most recess 198 as shown in FIG. 1F may contain a first dosage amount. The respective packages 200 in the central recess 198 as shown in FIG. 1F may contain a second dosage amount different from the first dosage amount of the respective package 200 in the left-most recess 198. The respective packages 200 in the right-most recess as shown in FIG. 1F may contain a third dosage amount different from the first dosage amount and the second dosage amount of the respective packages 200 in the other respective recesses 198.

Figure 1G:
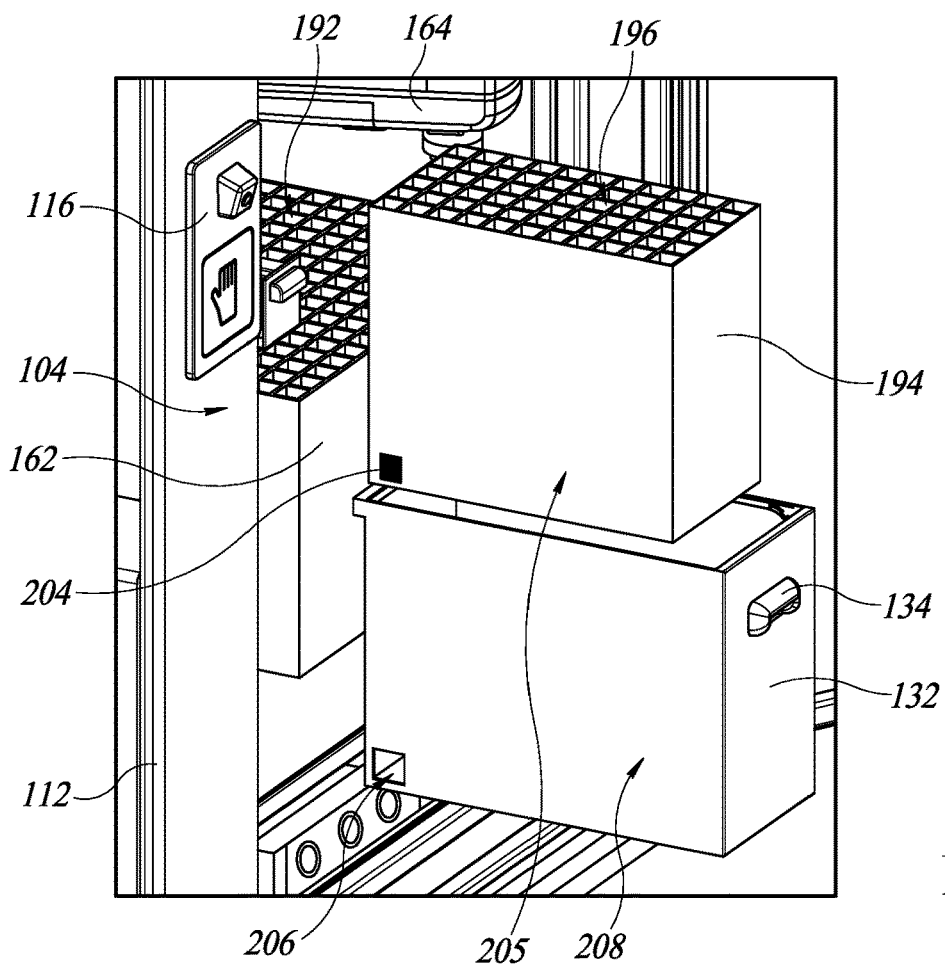
FIG. 1G is a zoomed in exploded view of a drawer system that extends into the internal chamber of the safe when closed.

FIG. 1G is a zoomed in exploded view of the first drawer 132 and the medication restock container 194 that may be removably received by the first drawer 132. As discussed earlier, the medication restock container 194 includes the matrix or array of the plurality of recesses 196. The medication restock container 194 further includes an identification label 204 on a second sidewall 205 of the medication restock container 194, which may be a barcode, radio frequency identification (RFID) tag, or some other type of identification readily visible on an external surface of the medication restock container 194.

The first drawer 132 that removably receives the medication restock container 194 further includes an opening 206 that extends through a third sidewall 208 of the first drawer 132. The opening 206 is aligned with and exposes the identification label 204 from the first drawer 132 when the medication restock container 194 is removably within the first drawer 132.

When the medication restock container 194 is within the first drawer 132 and the first drawer 132 is within the internal chamber 128 of the safe 124 as shown in FIGS. 1D and 1E, the identification label 204 is within a FOV of the second scanner 188, which may be readily seen in FIGS. 1D and 1E. Since the identification label 204 is exposed from the third sidewall 208 of the first drawer 132, the second scanner 188 may readily scan the identification label 204 for record keeping purposes or to select or provide restock control instructions to be communicated to the manipulator 164. For example, the second scanner 188 may scan the identification label 204 at which point the second scanner 188 may provide information to a memory external to or within the kiosk 100 (e.g., within the control box 184). The memory may then select and provide control instructions to be sent to the manipulator 164 to restock and refill the storage case 162 with the respective medication containers 158 in the plurality of recesses 196 in a selected order or in a selected manner. For example, the respective medication containers 158 in ones of the recesses 196 may be removed before other ones of the respective medication containers 158 in other ones of the recesses 196.

Figure 1I:
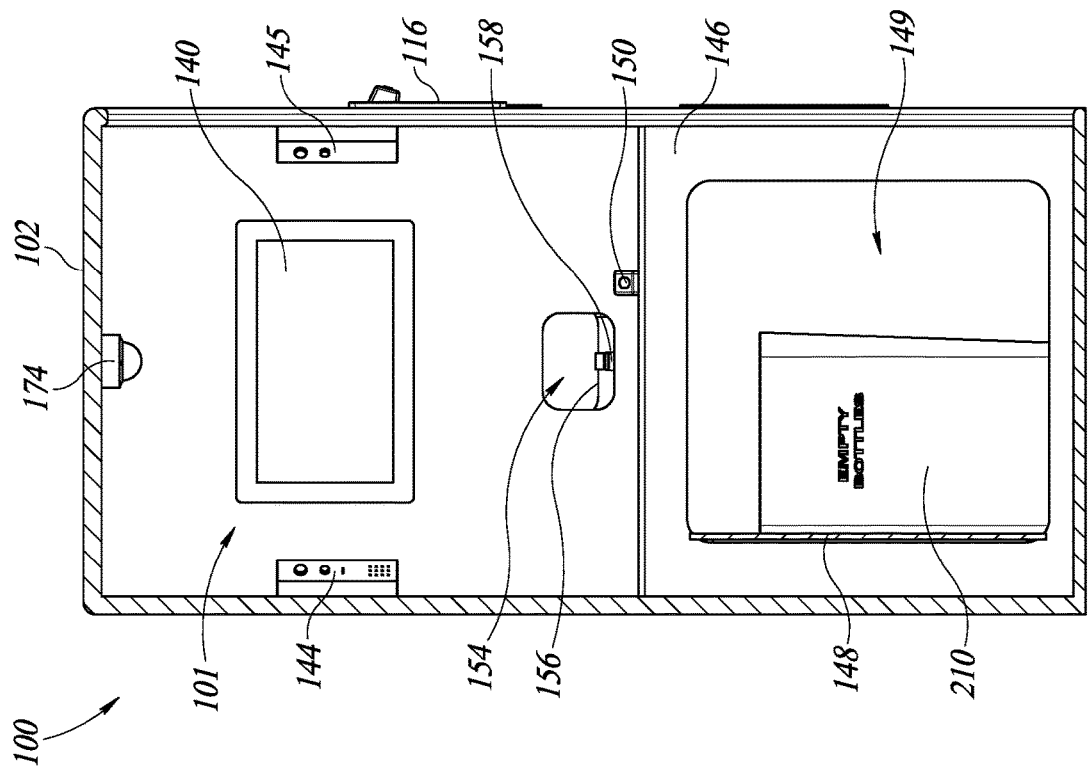
FIG. 1I is an interior view of the patient compartment of the embodiment of the kiosk as shown in FIGS. 1A and 1B with a door accessible in the patient compartment opened.
Figure 1H:
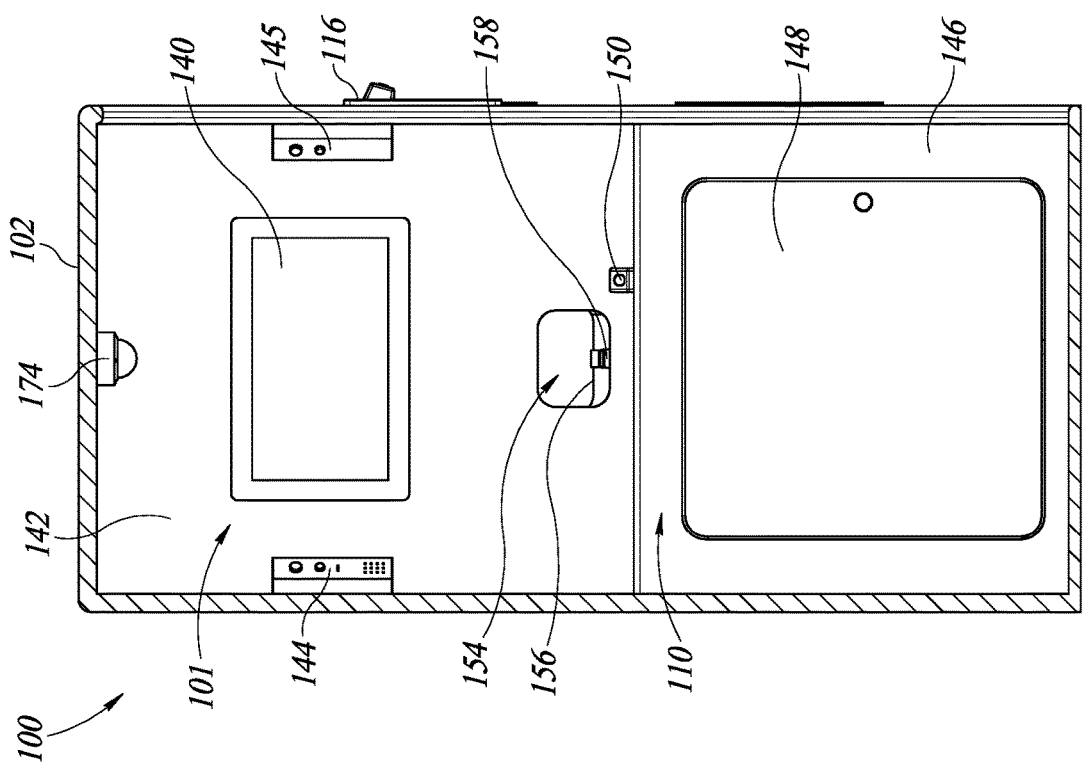
FIG. 1H is an interior view of a patient compartment of the embodiment of the kiosk as shown in FIGS. 1A and 1B.

FIG. 1H is an interior view of the patient compartment 101 of the embodiment of the kiosk 100 as shown in FIGS. 1A and 1B with the forth door 148 in a closed position. FIG. 1I is an interior view of the patient compartment 101 of the embodiment of the kiosk 100 with the fourth door 148 in an opened position.

As can readily be seen in FIG. 1H, a second audio component 145 is on and present at a respective corner of the patient compartment 101 opposite to the respective corner at which the first audio component 144 is on and present. The second audio component 145 may be the same or similar to the first audio component 144.

As can readily be seen in FIG. 1I, a bin 210 is within the compartment 149. The bin 210 may be a garbage can, a trash can, or some other type of waste can, bin, or storage container that may hold empty ones of the medication containers 158. After the patient takes their medication dispensed through the dispense opening 152, the medication container 158, which previously contained the patient's medication before ingestion and is now empty, is inserted into and passes through the one-way receptacle 152 into the bin 210. The empty medication container 158 enters the compartment 149 through the one-way receptacle and is dropped into the bin 210. Before or once the bin 210 is full, a maintenance employee may access the compartment 149 through the fourth door 148 by utilizing the second biometric scanner 150 to unlock the fifth lock, which locks the fourth door 148 in the closed position to limit access to the compartment 149. By disposing of empty ones of the medication containers 158 in this manner, confidential information on empty ones of the medication containers 158 is not readily accessible to other individuals besides a patient whom took the medication from the medication container 158.

Figure 1J:
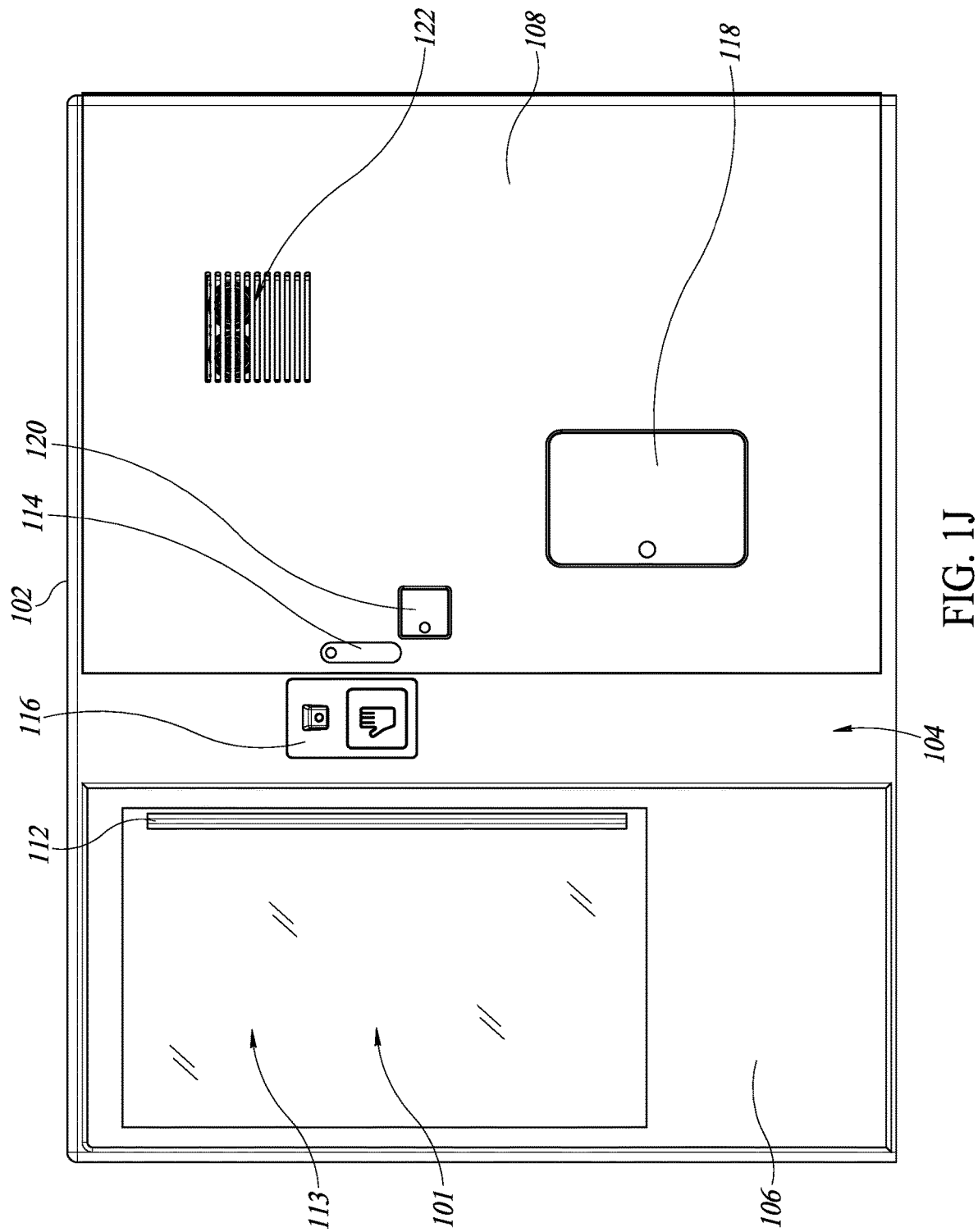
FIG. 1J is a front side view of the embodiment of the kiosk as shown in FIGS. 1A and 1B with the doors coupled to the chassis and the door of the safe closed.
Figure 1K:
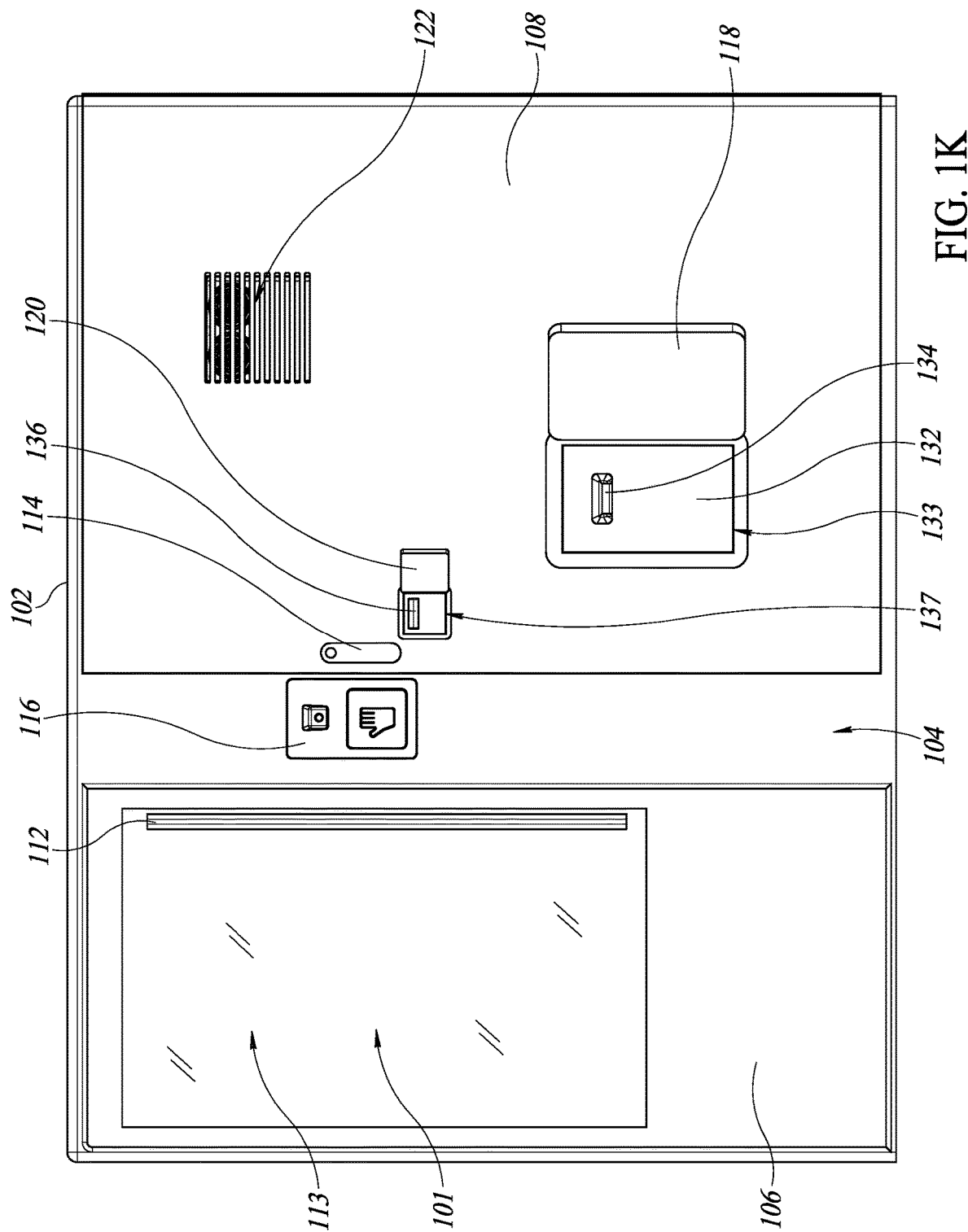
FIG. 1K is a front side view of the embodiment of the kiosk as shown in FIGS. 1A and 1B with the doors coupled to the chassis and the door of the safe closed, and with hatches on and in one of the doors of the chassis providing access to drawers extending into the safe and accessible through the hatches.

FIG. 1J is a front side view of the kiosk 100 when the first, second, and third doors 106, 108, 126, as well as the first hatch 118 and the second hatch 120, are in their closed positions. FIG. 1K is a front side view of the kiosk 100 when the first, second, and third doors 106, 108, 126 are in their closed position whereas the first and second hatches 118, 120 are in their opened positions to access the first drawer 132 and the second drawer 136, respectively.

When the first hatch 118 is in the opened position, the first drawer 132 may be readily accessed and removed through the first hatch 118. When the second hatch 120 is in the opened position, the second drawer 136 may be readily accessed and removed through the second hatch 120. The first and second drawers 132, 136, respectively, may be removed to be refilled and then reinserted into the respective openings 133, 137 when restocking medication to be stored within the internal chamber 128 of the safe 124.

For example, the first drawer 132 may be removed, then the medication restock container 194 may be removed from the first drawer 132, and a new medication restock container 194 already pre-filled with new ones of the medication containers 158 containing medication may be removably placed within the first drawer 132. After removably placing the new medication restock container 194 pre-filled with the respective medication containers 158, the first drawer 132 and the new medication restock container 194 are reinserted into the safe 124 through the opening 133. The manipulator 164 then takes the respective medication containers 158 out of the new medication restock container 194 and places them within the storage case 162. This process may be repeated multiple times to completely fill the storage case 162 with the respective medication containers 158. After the restock process is complete utilizing the first drawer 132, the first drawer 132 may be reinserted into the safe 124 through the opening 133 for a final time, the first hatch 118 may then be closed, and the first hatch 118 may then be locked into the closed position by the fourth lock.

In some embodiments, the manipulator 164 may remove ones of the medication containers 158 within the storage case 162 when the medication in ones of the medication containers 158 is expired or out of date. For example, the end effector of the manipulator may pick up a respective medication container 158 containing expired or out of date medication and may transfer the respective medication container 158 into the medication restock container 194. The respective medications container 158 with the expired or out of date medication, which is in the medication restock container 194, may be removed from the kiosk 100 by a maintenance employee at the beginning of performing the restocking process as described above.

Similar to the first drawer 132, the second drawer 136 may be removed and then new ones of the packages 200 may be placed within the plurality of recesses 198 to restock the second drawer 136. After the new ones of the packages 200 are placed within the plurality of recesses 198, the second drawer 136 is then reinserted into the safe 124 through the opening 137. After the second drawer 136 has been reinserted, the second hatch 120 is closed and locked into the closed position by the fourth lock.

While the packages 200 are being described as containing medication in a strip form, in some embodiments, the packages 200 may instead contain medication patches that are applied to the skin. For example, the patient may open a respective package 200 and apply a medication patch to their skin to assist in treatment or treat an ailment of the patient.

An embodiment of a method of a patient obtaining their medication utilizing the kiosk 100 is set forth as follows. A patient approaches the kiosk 100, opens the first door 106, and enters the kiosk 100. After the patient enters the kiosk 100, the patient may interact with a touchscreen of the video conference display 140 to initiate an interaction with a medical professional (e.g., nurse, doctor, or some other certified medical professional) through the video conference display 140. The medical professional may have a discussion with the patient to ask them some medical questions and confirm their identity.

After the medical professional confirms the patient's identity through the image of the patient over the video conference display 140 as well as by asking questions to confirm the patient's social security information, driver's license information, or some other confidential information known only by the patient, the medical professional may send an electrical signal (e.g., control signal or instruction) to the kiosk 100 to initiate operation of the manipulator 164. During operation, an end effector of the manipulator 164 picks up one of the respective medication containers 158 stored within one of the plurality of recesses 192 of the storage case 162. The manipulator 164 then articulates and actuates to move the respective medication container 158 such that the respective medication container 158 is aligned with and over the reception opening 202 of the dispense structure 156 while being gripped by the end effector of the manipulator 164.

After the medication container 158 is aligned with and over the reception opening 202, the end effector of the manipulator 164 releases the medication container 158 and drops the respective medication container 158 into the reception opening 202. The respective medication container 158 then passes through the dispense structure 156 such that the respective medication container 158 is accessible to the patient in the patient compartment 101 through the dispense opening 154.

Before the manipulator 164 aligns the respective medication container 158 over the reception opening 202, a label may be applied to the respective medication container utilizing the printer 168. For example, the printer 168 may print a label having one side covered by an adhesive. The manipulator 164 may then bring the respective medication container 158 to the label, and the label may be adhered to the respective medication container 158 by the manipulator 164 pressing the respective medication container 158 against the side of the label covered in the adhesive.

Before the manipulator 164 aligns the respective medication container 158 over the reception opening 202, a label present on the respective medication container 158 may be scanned by the scanner 170 for record keeping purposes. For example, the manipulator 164 may move a label on the respective medication container 158 within the FOV of the scanner 170 at which point the scanner 170 scans an identifier (e.g., barcode, RFID tag, QR code, etc.) on the respective medication container 158 for record keeping purposes.

Before the manipulator 164 aligns the respective medication container 158, the first camera 172 may capture an image of a label on the respective medication container 158, may capture an image of the respective medication container 158, or may capture an image of both of the label and the respective medication container 158 for record keeping purposes. For example, the manipulator 164 may move a label on the respective medication container 158 or the respective medication container 158 within the FOV of the first camera 172 at which point the first camera 172 captures an image of the label on the respective medication container 158, captures an image of the respective medication container 158, or captures an image of both for record keeping purposes.

After the patient has obtained the respective medication container 158, the patient then opens the respective medication container 158 at which point the patient ingest the medication within a FOV of the camera of the video conference display 140 and/or the first surveillance camera 174. By ingesting the medication within the FOV of the video conference display, the first surveillance camera 174, or both, the medical professional observes ingestion of the medication by the patient to readily confirm ingestion of the medication from the respective medication container 158 by the patient to reduce the likelihood of diversion of the medication by the patient. The video conference display 140 and/or the first surveillance camera 174 may record the patient while the patient is within the patient compartment 101 to observe and confirm ingestion of the medication by the patient to reduce the likelihood of diversion of the medication by the patient. The video conference display 140, the first surveillance camera 174, or both may be outfitted with a thermal imager or a thermal image camera to confirm ingestion of the medication by the patient to reduce the likelihood of diversion of the medication by the patient.

When the video conference display 140, the first surveillance camera 174, or both have a thermal image camera(s), the thermal image camera(s) is utilized to monitor whether the patient has ingested the medication to avoid diversion of the medication. Since the medication stored within the medication compartment 110 is maintained at the selected temperature by the temperature adjustment module 130, the thermal image camera is configured to monitor and track the ingestion of the medication at the selected temperature by the patient.

In some embodiments, the medication within the medication compartment 110 is stored at the selected temperature, which is colder than the ambient temperature within the patient compartment 101, and the thermal image camera follows and tracks the medication (e.g., pill, liquid, etc.) at the selected temperature by outputting a heat map to a display that is visible to the medical professional who is dispensing the medication and monitoring ingestion of the medication by the patient from a remote location. Since the medication is at the selected temperature that is colder than the ambient temperature, the medication is represented by a blue color output by the thermal image camera to the display visible by the medical professional at the remote location to assist in confirming ingestion and avoiding diversion. To confirm ingestion and avoid diversion of the medication, shortly after the patient has inserted the medication into their mouth and ingested (e.g., swallowed) the medication in relatively short succession, the medical professional will generally request that the patient open their mouth and lift their tongue to confirm that the medication was ingested by the patient by confirming no blue color is within the mouth of the patient or underneath the patient's tongue utilizing the heat map output by the thermal image camera in real time.

In some embodiments, the thermal image camera may be sensitive enough to detect the medication at the selected temperature even when the patient's mouth is closed such that ingestion of the medication at the selected temperature may be monitored in real time. For example, the thermal image camera may be sensitive enough to output a blue color representative of the medication through the patient's mouth even when the patient's mouth is closed and containing the medication, and, as the patient ingests (e.g., swallows), the thermal image camera may be sensitive enough to track the medication at the selected temperature passing through the esophagus of the patient to avoid diversion by the patient hiding the medication in their mouth.

In some embodiments, a thermal imager or a thermal imaging device (not shown), which may be a thermal image camera, may be provided in the kiosk 100 that is separate and distinct from the video conference display 140 and the first surveillance camera 174, and the thermal imager (not shown) may be utilized to monitor the patient compartment 101 of the kiosk 100. For example, the thermal imager may include one or more thermal imaging cameras to monitor ingestion of the medication at the selected temperature by the patient within the patient compartment 101. In some embodiments, one or more thermal imagers, thermal imaging devices, or thermal imaging cameras may be provided at different locations to monitor the patient compartment 101 of the kiosk 100 from multiple angles and perspectives to avoid diversion of the medication. When the thermal imager is sensitive enough to track the medication passing through the esophagus of the patient, the thermal imager with greater sensitivity provides the medical professional at the remote location with the capability to confirm consumption and ingestion of the medication by the patient within the patient compartment 101 even when the patient may be haphazard, confrontational, or having some other type of difficulty communicating fully or cordially with the medical professional at the remote location.

In an alternative embodiment of the method, the medication container 158 may not be released by the end effector of the manipulator 164 until the patient confirms their identity utilizing the second biometric scanner 150. For example, if the second biometric scanner 150 is a finger print scanner, before the respective medication container 158 is released by the end effector of the manipulator 164 into the reception opening 202, the patient confirms their identity by scanning their fingerprint utilizing the second biometric scanner 150. After the patient's identity has been confirmed by scanning their fingerprint on the second biometric scanner 150, the end effector of the manipulator 164 releases the respective medication container 158 in response to the confirmation of the identity of the patient utilizing the second biometric scanner 150. In other words, the end effector of the manipulator 164 only releases the respective medication container 158 in response to confirmation of the patient's identity utilizing the second biometric scanner 150. To increase security and reduce the likelihood of theft or misappropriation of the medication due to identity theft, the second biometric scanner 150 may be a combination of scanners such as a retinal scanner, a fingerprint scanner, a blood scanner, or some other type of biometric scanner. In other words, the second biometric scanner 150 may be a plurality of biometric identification options that may be used in combination to ensure or minimize tampering or unauthorized acquisition of the medication (e.g., pharmaceutical agents) stored within the kiosk 100.

The patient's identity may be confirmed by comparing the finger print of the patient utilizing the second biometric scanner 150 to encrypted secure identifiable information on a memory within the kiosk 100 such that when an authorized patient scans their finger print with the second biometric scanner 150 the end effector of the manipulator 164 releases the medication container 158 into the reception opening 202. After the medication container 158 is released into the reception opening 202, the authorized patient may access the medication container 158 through the dispense opening 154. The manipulator 164 will be configured to only dispense the medication container 158 to the authorized patient after secure identification of the authorized patient has been confirmed by comparing the fingerprint scanned by the second biometric scanner 150 to the encrypted secure identifiable information stored on the memory.

Alternatively, the encrypted secure identifiable information may be stored remotely in a cloud in electrical communication (e.g., wired, wireless, or some combination of wired and wireless electrical connections). The manipulator 164 will be configured to only dispense the medication (e.g., pharmaceutical agent) container 158 to the authorized patient after secure identification of the authorized patient has been confirmed by comparing the finger print scanned by the second biometric scanner 150 to the encrypted secure identifiable information stored in the cloud, which may be external to the kiosk 100.

In an alternative embodiment of the method, the medical professional may have remote control over the manipulator 164. For example, the medical professional may use a remote control to provide instructions to the manipulator 164. In at least one situation, the medical professional may provide a pick up medication container instruction to the manipulator 164 in which the end effector of the manipulator 164 picks up one of the respective medication containers 158 in the storage case 162 and transfers the respective medication container 158 to be aligned with and over the reception opening 202. After the respective medical container 158 is aligned with and over the reception opening 202, the medical professional may provide a dispense medication container instruction to the manipulator 164 wherein the end effector of the manipulator 164 releases the respective medication container 158 into the reception opening 202 to dispense the respective medication container 158 to a patient in the patient compartment 101 through the dispense structure 156.

In an alternative embodiment of the method, instead of sending an electrical signal (e.g., control signal or instruction) to the manipulator 164, the medical professional may instead send an electrical signal (e.g., control signal or instruction) to the kiosk 100 to initiate operation of the actuator 186. In some embodiments, the actuator 186 may not dispense the package 200 into the reception opening 202 until the patient has confirmed their identity utilizing the second biometric scanner 150. For example, if the second biometric scanner 150 is a finger print scanner, before the respective package 200 is released by the end effector of the actuator 186 into the reception opening 202, the patient confirms their identity by scanning their fingerprint utilizing the second biometric scanner 150. After the patient's identity has been confirmed by scanning their fingerprint on the second biometric scanner 150, the end effector of the actuator 186 releases the respective medication container 158 in response to the confirmation of the identity of the patient utilizing the second biometric scanner 150. In other words, the end effector of the actuator 186 only releases the respective medication container 158 in response to confirmation of the patient's identity utilizing the second biometric scanner 150.

In an alternative embodiment of the method, the patient may need to scan their fingerprints or handprint on the first biometric scanner 116 before being permitted access to utilize the kiosk 100. For example, the video conference display may not turn on such that the patient cannot initiate the interaction with the medical professional to obtain their medication utilizing the kiosk 100. To increase security and reduce the likelihood of theft, misappropriation, or unauthorized acquisition of the medication due to identity theft, the first biometric scanner 116 may be a combination of scanners such as a retinal scanner, palm scanner, a fingerprint scanner, a blood scanner, a DNA identification scanner, facial recognition scanner, or some other type of biometric scanner. In other words, the first biometric scanner 116 may be a plurality of biometric identification options that may be used in combination to ensure or minimize tampering or unauthorized acquisition of the medication (e.g., pharmaceutical agents) stored within the kiosk 100.

Figure 2A:
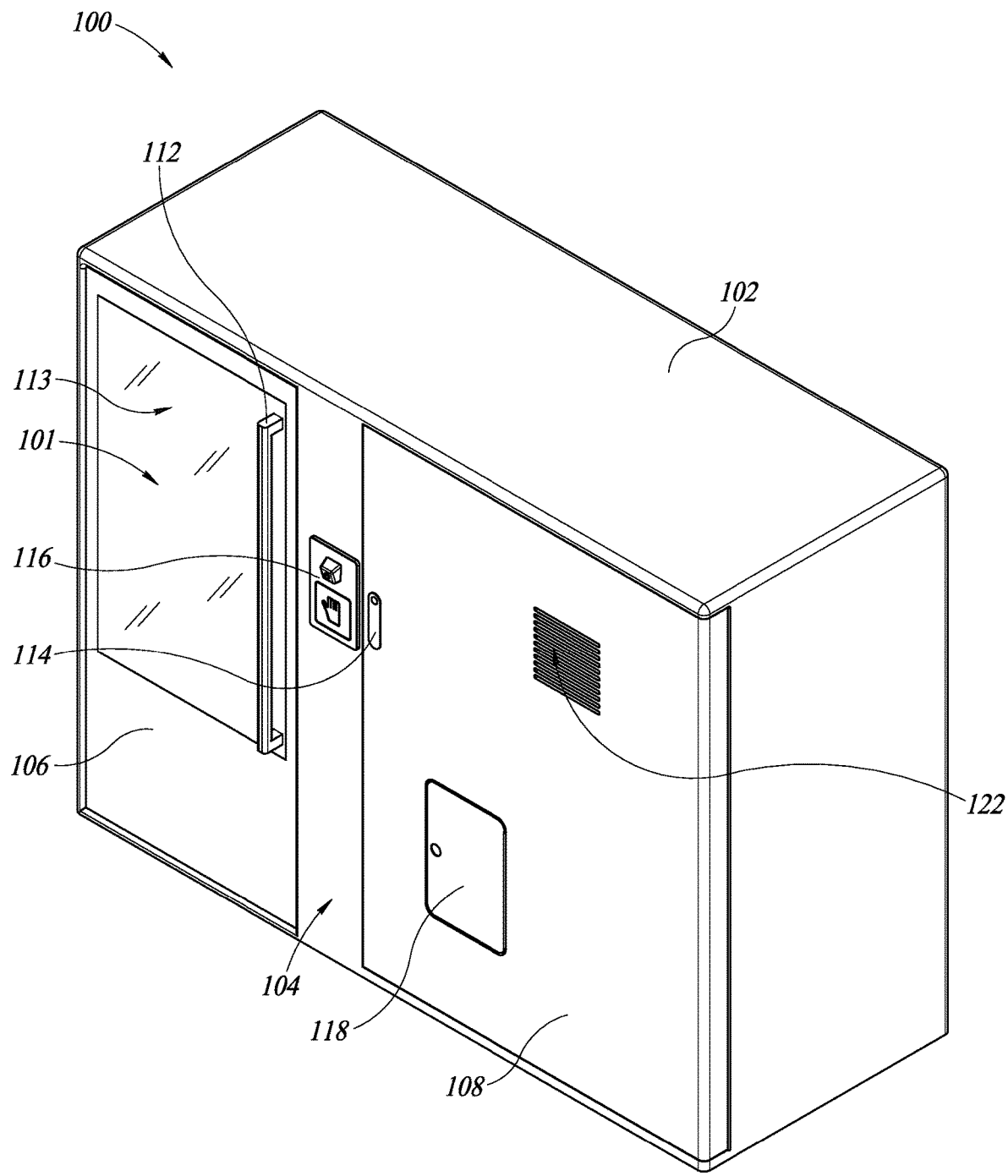
FIG. 2A is a perspective view of an alternative embodiment of a kiosk of the present disclosure.
Figure 2B:
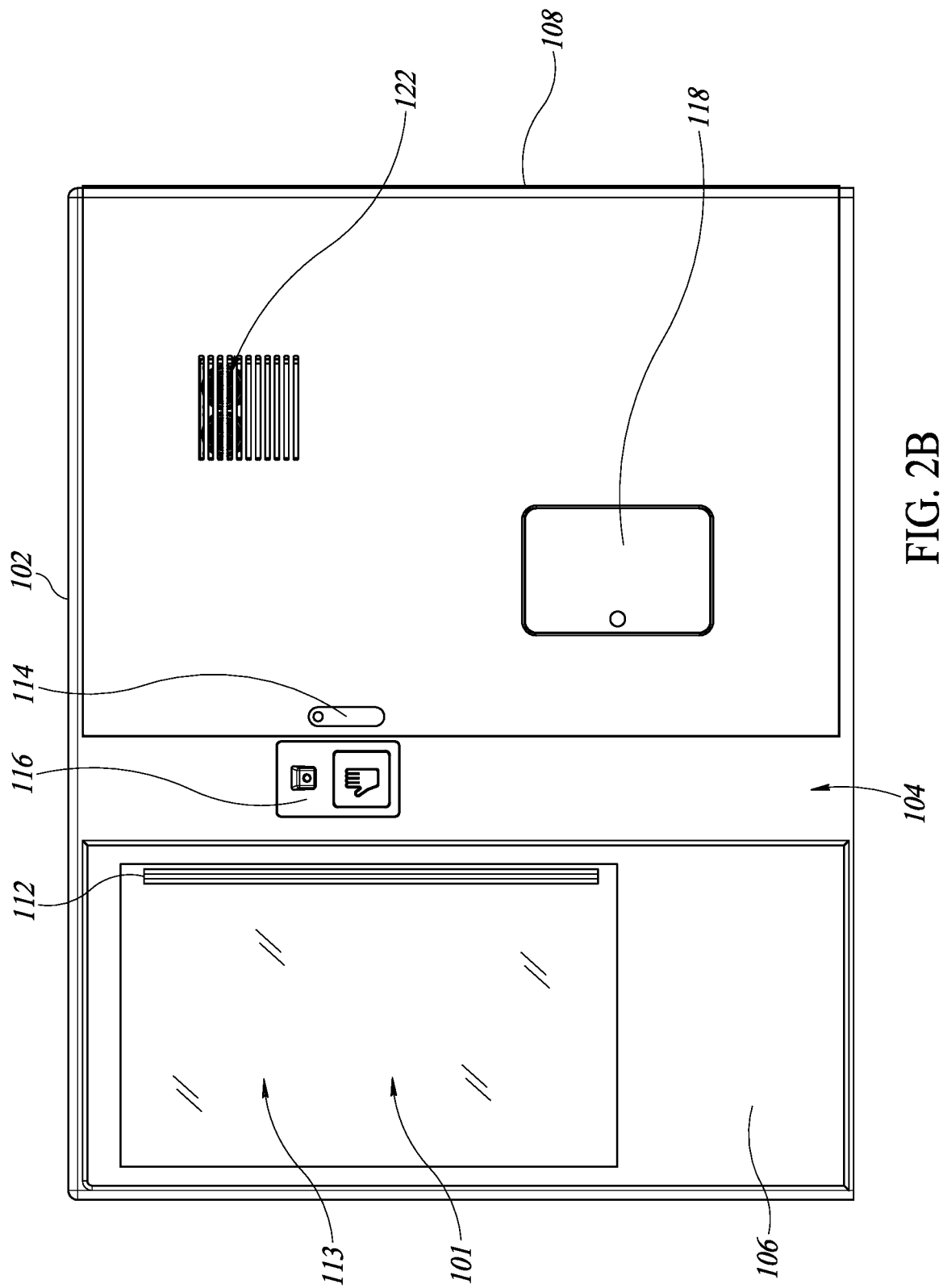
FIG. 2B is a front view of the alternative embodiment of the kiosk as shown in FIG. 2A.
Figure 2C:
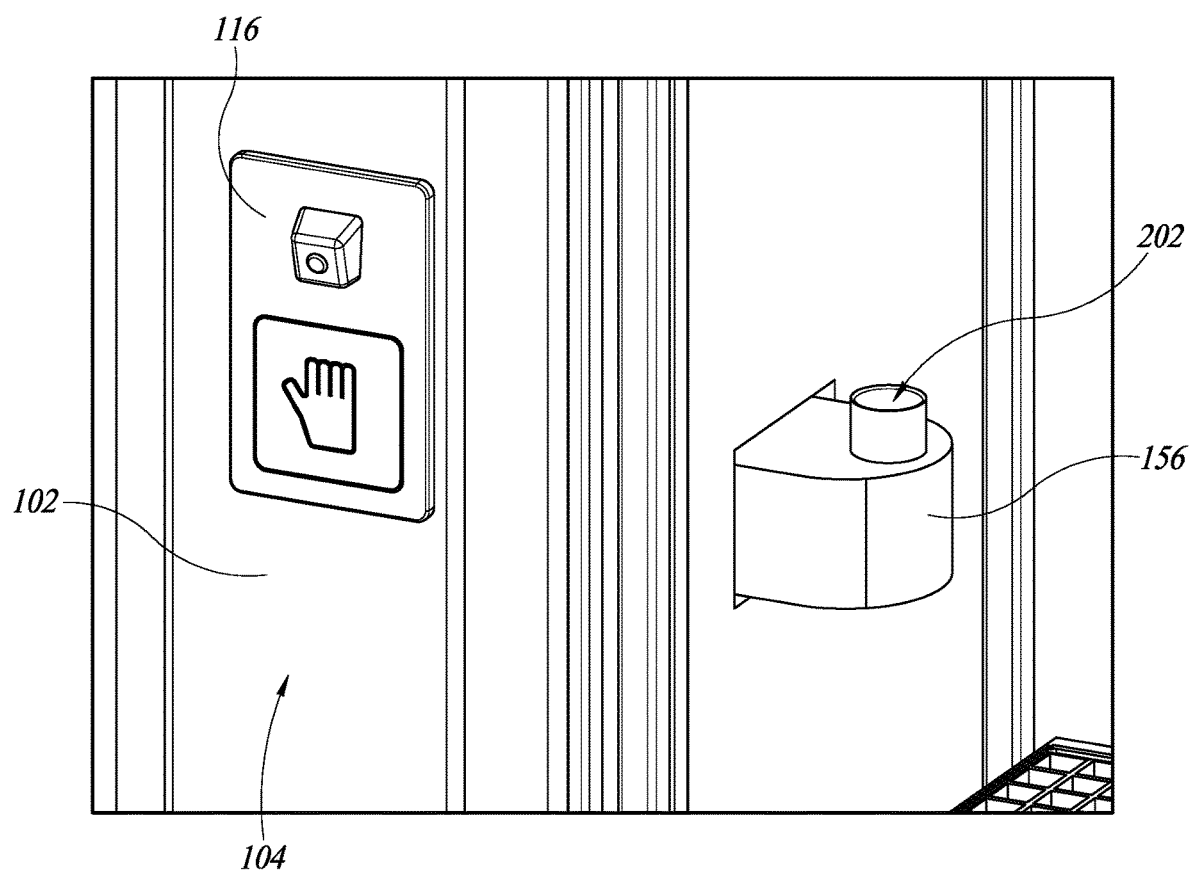
FIG. 2C is a zoomed in view of a component within an internal chamber of a safe of the alternative embodiment of the kiosk as shown in FIGS. 2A and 2B.

FIGS. 2A and 2B are directed to an alternative embodiment of the kiosk 100 without the second hatch 120, the second drawer 136, and the actuator 186. FIG. 2C is a zoomed in view of the dispense structure 156 when the second drawer 136 and the actuator 186 are not present in this alternative embodiment of the kiosk 100.

In some embodiments of the kiosk 100, some or all of the locks as described with respect to the above embodiments of the kiosk 100 of the present disclosure may be key locks instead of mechanical locks or electro-mechanical locks that are unlocked utilizing a biometric scanner. In some embodiments of the kiosk 100, some or all of the locks as described with respect to the embodiments of the kiosk 100 of the present disclosure may be a combination of key locks (e.g., unlocked by keys) and electro-mechanical locks (e.g., unlocked by the first or second biometric scanners 116, 150, respectively). Alternatively, in some alternative embodiments of the kiosk 100, there may be more locks for limiting access to other various areas of the embodiments of the kiosk 100 to properly secure and limit access to areas of the embodiments of the kiosk 100 to avoid misappropriation or unauthorized acquisition (e.g., theft by breaking into the kiosk 100) of medication stored within the embodiments of the kiosk 100.

In some embodiments of the kiosk 100, there may be additional surveillance cameras to the first and second surveillance cameras 174, 176 to increase security of the embodiments of the kiosk 100 to reduce the likelihood of diversion or misappropriation of the medication stored within the kiosk 100. For example, additional surveillance cameras may be positioned on the external surface 104 of the embodiments of the kiosk 100 to increase security of the kiosk 100 to reduce the likelihood of diversion or misappropriation of the medication stored within the kiosk 100.

In some embodiments of the kiosk 100, the first surveillance camera 174 may be one of multiple surveillance cameras within the patient compartment 101. For example, the first surveillance camera 174 may be oriented to record the full body of the patient, and another surveillance camera may be mounted on the wall 142 in the patient compartment 101 oriented to record the upper body of the patient. There may be even another surveillance camera mounted to the shelf 146 and may be oriented to record the lower body of the patient within the patient compartment 101.

Figure 3:
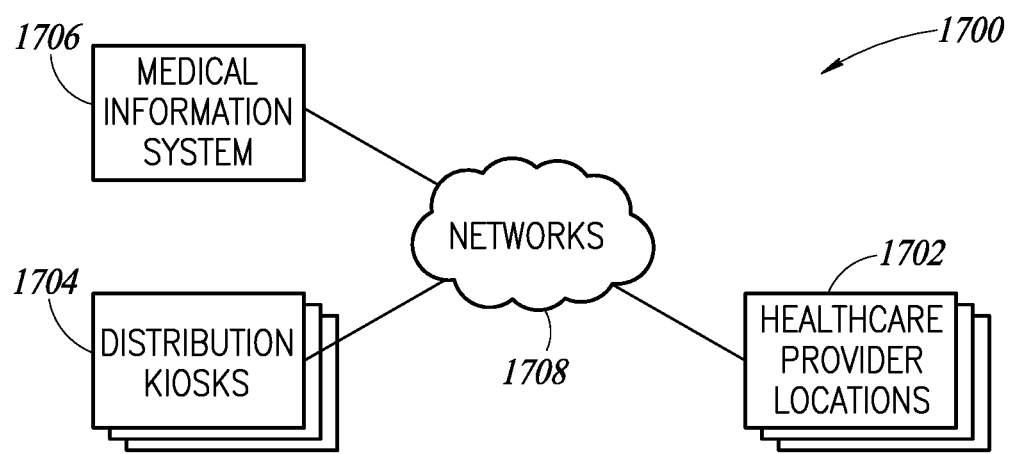
FIG. 3 is a block diagram of a medical treatment system 1700, according to one embodiment.

FIG. 3 is a block diagram of a medical treatment system 1700, according to one embodiment. The medical treatment system 1700 includes healthcare provider locations 1702, distribution kiosks 1704, and an information system 1706. The healthcare provider location 1702, the distribution kiosks 1704, and information system 1706 are communicatively coupled together by one or more networks 1708. The components of the medical treatment system 1700 cooperate together to provide medical services to individuals. The distribution kiosks 1704 may be any one of the kiosks or combinations of the kiosks described within the present disclosure or within the scope of the present disclosure. For example, the distribution kiosks 1704 may include kiosks the same or similar to the kiosk 100 as shown in FIGS. 1A-1K and may include kiosks the same or similar to the kiosk 200 as shown in FIGS. 2A-2C.

In one embodiment, the healthcare provider locations 1702 can include hospitals, medical clinics, pharmacies, urgent care centers, emergency rooms, or other locations or venues at which healthcare professionals may provide healthcare services to individuals. The healthcare provider locations 1702 include computing resources. The computing systems can include processing resources, memory resources, data transmission resources, displays, input devices, or other systems and devices that may be utilized by healthcare professionals. For example, some of these devices may be present within the control box 184 of the kiosk 100.

In one embodiment, the computing systems can store medical information related to patients that utilize the services of the healthcare professionals. The medical information can include personal identification information such as names of patients, addresses of patients, insurance information of patients, birthdates of patients, government identification numbers of patients, biometric identification information, or other types of personal identification information associated with patients. The medical information can also include medical history information. The medical history information can include data related to previous medical conditions of patients. The medical history information can include information related to previous or ongoing ailments, injuries, sicknesses, diagnoses, treatments, surgeries, allergies and medications. This information may be stored in one or more databases in computer memories at least partially located at the healthcare provider location. The medical information may include the patient identification profile, including fingerprints, retinal scans, or any other biometric identifier suitable for these applications.

In one embodiment, an individual may consult a healthcare professional, such as a physician. The physician may make a diagnosis of a condition of the individual, such as opioid use disorder (OUD). The physician may prescribe a medication to the user to be administered to the user, such as strips of the medication (e.g., pharmaceutical agents) described above, among other treatments. The physician may distribute or provide the medication (e.g., pharmaceutical agent) to the user utilizing the manipulator 164 of the kiosk. Alternatively, the physician may indicate that the medication is to be provided or distributed to the user from a healthcare professional of a separate healthcare provider location. In one example, the second healthcare provider location is an online specialty pharmacy or addiction treatment facility.

In one embodiment, the physician, or another healthcare professional associated with the physician, may record details of the diagnosis and prescription in the computing systems of the healthcare provider locations. The details can include a name of the medication, dosage levels to be administered, a schedule for adjusting dosage levels, a number of allowable refills of the medication, contingencies for replacing the medication with a second medication, dosage levels of the second medication, and other details related to the medical condition of the individual, the diagnosis, and the prescription. If the physician provides the pharmaceutical agent to the user, then the physician or other healthcare professional may record, in the computing systems, an identification of the pharmaceutical agent.

In one embodiment, after receiving the diagnosis from the physician, the individual may go to one of the kiosks at a pharmacy or some other location at which the kiosk is present to obtain the pharmaceutical agent utilizing the kiosk. The pharmacist, or another healthcare professional, may provide or distribute the pharmaceutical agent to the user utilizing the manipulator within the kiosk. The pharmacist or other healthcare professional may record, with computing systems associated with the pharmacy, details related to the individual, the diagnosis of the individual, the prescription, medical history of the individual, details related to the pharmaceutical agent, or other suitable information. This information may be stored at least partially in databases implemented, at least partially, in computer memories located at the pharmacy.

In one embodiment, some of the information associated with the individual may be stored with the medical information system 1706. The medical information system 1706 can include computing resources including, but not limited to servers, processing resources, memory resources, and data transmission resources. The medical information system 1706 can include physical and virtual computing resources.

In one embodiment, the medical information system 1706 can be, at least partially, a cloud-based medical information system. The medical information system 1706 can include medical information databases, medical information applications, and other medical information resources implemented with the computing resources. These databases, applications, and resources may be implemented partially or entirely in the cloud. These databases, applications, and resources may be accessible via the cloud.

In one embodiment, the previously mentioned information stored in association with the healthcare provider location 1702 may be partially or entirely stored in the medical information system 1706. In other words, personal identification information (e.g., biometric identification information), medical history information, diagnosis information, treatment information, prescription information, or other information associated with individuals that is recorded at the healthcare provider location 1702 may be stored in the medical information system 1706. Some or all of the information may be duplicated at the healthcare provider location 1702 and the medical information system 1706. Alternatively, some or all of the information recorded at the healthcare provider locations may only be stored with the medical information system 1706.

In one embodiment, the medical information system 1706 and the computing systems of the healthcare provider locations 1702 may share software applications. The shared software applications may enable data stored at a healthcare provider location 1702 to be automatically sent to them recorded in the medical information system 1706. Likewise, the shared software applications may enable healthcare providers at the healthcare provider location 1702 to retrieve medical information related to individuals or devices from the medical information system 1706.

In one embodiment, an individual that is to ingest a pharmaceutical agent based on the prescribed treatment will visit one of the distribution kiosks 1704 in order to receive and ingest their prescribed treatment (e.g., prescribed dosage of medication). For example, in one instance, the user (e.g., patient) may receive and ingest their medication at one of the distribution kiosks 1704 at a first location, and, in another instance at a later time, may receive and ingest their medication at another one of the distribution kiosks 1704 at a second location different from the first location.

In one embodiment, the distribution kiosks include computing resources such as processing resources, memory resources, data transmission resources, or other types of computing resources. These resources may be in the control box 184 or may be in second portion 128*b* of the internal chamber 128 of the safe 124. These computing resources can receive, process, and store data related to pharmaceutical agent that have been provided to individuals. The computing resources of the distribution kiosks 1704 can include personal identification information (e.g., biometric identification information), medical history information, and current diagnosis and prescription information associated with individuals. The computing resources of the distribution kiosks 1704 may include databases that store these types of information. Various encryption and data security methods will be implemented to ensure safe storage of any personal information to reduce the likelihood of misappropriation or theft by an individual unauthorized to access the personal information. In some embodiments, the personal information will not be permanently stored in the kiosk and instead will only be accessed and temporarily saved at the kiosk when needed to interact with that patient.

In one embodiment, the computing resources of the distribution kiosks 1704 can assist in implementing security measures related to the distribution kiosks. For example, the computing resources of the distribution kiosks 1704 can assist in authenticating individuals and referencing databases to ensure that individuals are authorized to receive the medication utilizing the kiosk. The computing resources can assist in ensuring that the identification of a medication that a user seeks corresponds to the medication that was legitimately prescribed to the user by a medical professional. If the identity of the patient or the identification of the medication (e.g., pharmaceutical agent) does not match, then the distribution kiosk 1704 may refuse to distribution of the pharmaceutical agent to the potentially unauthorized patient. The medication may be identified by scanning a label on one of the medication containers 158 in which the medication (e.g., pharmaceutical agent) is stored.

In one embodiment, the computing resources of the distribution kiosks 1704 may assist in obtaining and analyzing current physical indicators of the user. These indicators may include heart rate, blood pressure, pupil dilation characteristics, body temperature, facial features, or other indicators of the current physical state of the user. The distribution kiosks 1704 may include sensors to sense these physical indicators. The computing resources of the distribution kiosks 1704 may then assist in performing diagnostics based on the sensed physical indicators. In other words, these computing resources are generally within the kiosks 100, 200 to obtain, monitor, and analyze the physical indicators of the user (e.g., patient).

In one embodiment, the computing resources of the distribution kiosks 1704 may include one or more machine learning-based analysis models. The machine learning-based analysis models may be trained, with one or more machine learning processes, to determine whether a user should receive the medication container 158 containing the user's particular prescribed medication (e.g., prescribed dosage and type of medication). The machine learning processes may train the analysis model to make these determinations based on the current physical indicators of the user.

In one example, when a user accesses a distribution kiosk 1704 to attempt to receive and ingest their prescribed medication, sensors of the distribution kiosk 1704 may sense current physical indicators of the user. These current physical indicators may pass to the analysis model. The analysis model may determine that based on the current physical state of the user, the user should not receive. Instead, the analysis model may determine that the user should receive a different medication container with a different type of medication, or that the user should not receive any medication at all.

In one embodiment, the distribution kiosks 1704 stored data related to the diagnosis and prescription of individuals. When a user receives a medication from the distribution kiosks 1704, the distribution kiosk 1704 encodes medication distribution parameters based on the diagnosis and prescription information. This can include dosage rates, dosage timings, or other data related to the distribution of the medication.

In one embodiment, the distribution kiosk 1704 stores the same types of data as previously described related to the healthcare provider location 1704 and the medical information 1706. The databases of the distribution kiosks 1704 may store all of this data, part of this data, or other types of data not stored at all in the healthcare provider locations 1704 and the medical information system 1706. The computing resources of the distribution kiosks 1704 may implement software applications that communicate with the healthcare provider location 1702 and the medical information system 1706 in order to retrieve information from the healthcare provider locations 1702 and the medical information system 1706.

In one embodiment, the networks 1708 enable communication between the computing systems of the healthcare provider locations 1702, the computing resources of the distribution kiosks 1704, and the medical information system 1706. The networks 1708 can include the combination of one or more of local area networks, wireless area networks, cellular networks, satellite communication networks, the Internet, or other types of communication networks.

In one embodiment, healthcare provider location 1702 retrieve, when needed, medical data from the medical information system 1706 related to patients rather than storing that data permanently. The healthcare provider location 1702 can also provide data to the medical information system 1706 and to the distribution kiosk 1704. The networks 1708 enable this retrieval and transmission of data.

In one embodiment, when a user attempts to access a distribution kiosk 1704, the distribution kiosk 1704 retrieves data related to the user and/or the medication container 158 or package containing a medication to be distributed to the user from one or both of the healthcare provider location 1702 and the medical information system 1706. The distribution kiosks 1704 may also provide data related to a transaction with a user to one or both of the healthcare provider location 1702 and the medical information system 1706. The distribution kiosks 1704 transmit and receive this information via the networks 1708.

While the first and second biometric scanners 116, 150 are described as being finger print scanners, the first and second biometric scanners 116, 150 may alternatively be, but are not limited to, a handprint scanner, a palm veins scanner, a DNA identification scanner, a face-recognition scanner, a retina identification scanner, or some other type of biometric identification scanner. Alternatively, the first and second biometric scanners 116, 150 may be replaced with some other verification process or system such as, but not limited to, a multi-source identification software, a personal identification number, or any combination of the foregoing options as set forth herein.

A kiosk may be summarized as including a chassis including: an external surface; a patient compartment within the chassis; and a medication compartment within the chassis; a safe in the medication compartment, the safe including: an first internal chamber within the safe; and a first door that limits access to the first internal chamber within the safe; a second door coupled to the chassis, the second door limits access to the medication compartment and the first door of the safe; a third door coupled to the chassis, the third door limits access to the patient compartment; a first lock in mechanical cooperation with the first door; a second lock in mechanical cooperation with the second door; and an external biometric scanner accessible at the external surface of the chassis and in electrical communication with the first and second locks, the biometric scanner configured to unlock the first and second locks.

The kiosk may further include a wall between the patient compartment and the medication compartment, the wall limits access to the medication compartment and the safe through the patient compartment.

The kiosk may further include a dispense structure extending from the patient compartment to the first internal chamber of the safe, the dispense structure including a first end and a second end opposite to the first end, the dispense structure in fluid communication with the first internal chamber through the second end; and a dispense opening in fluid communication with the patient compartment and in fluid communication with the dispense structure through the first end.

The kiosk may further include a surveillance camera within the patient compartment; a video conference display within the patient compartment; a thermal imager within the patient compartment; a dispense structure accessible through the patient compartment, the dispense structure in fluid communication with the patient compartment and the first internal chamber; a one-way receptacle accessible within the patient compartment; a speaker within the patient compartment; and an internal biometric scanner within the patient compartment.

The kiosk may further include a fourth door within the patient compartment; a second internal chamber covered by the fourth door and accessible through the fourth door; and a third lock in mechanical cooperation with the fourth door.

The kiosk may further include a manipulator within the first internal chamber; a temperature adjustment module within the first internal chamber, the temperature adjustment module in fluid communication with an environment external to the first internal chamber and the chassis; a medication container storage case within the first internal chamber of the safe; and a surveillance camera within the medication compartment.

The kiosk may further include a medication container camera within the internal chamber; a label printer within the internal chamber; and an identification device within the internal chamber.

The kiosk may further include a medication restock drawer accessible through the first door.

The kiosk may further include a first surveillance camera within the patient compartment; a video conference display within the patient compartment; a thermal imager within the patient compartment; a dispense structure accessible through the patient compartment, the dispense structure in fluid communication with the patient compartment and the first internal chamber; a one-way receptacle accessible within the patient compartment; a speaker within the patient compartment; an internal biometric scanner within the patient compartment; a manipulator within the first internal chamber; a temperature adjustment module within the first internal chamber, the temperature adjustment module in fluid communication with an environment external to the first internal chamber and the chassis; a medication container storage case within the first internal chamber of the safe; and a second surveillance camera within the medication compartment.

A kiosk may be summarized as including a chassis including a patient compartment within the chassis and an external surface; a first biometric scanner on the external surface of the chassis; a first camera within the patient compartment; a video conference display within the patient compartment; a thermal imager within the patient compartment; a medication dispense structure accessible in the patient compartment; a one-way receptacle accessible in the patient compartment; and a first door coupled to the chassis limits access to the patient compartment.

The chassis may further include a medication compartment separate and distinct from the patient compartment; a safe in the medication compartment, the safe including an internal chamber communicatively coupled to the patient compartment by the medication dispense structure; a second door coupled to the chassis limits access to the medication compartment; and a second lock in mechanical cooperation with the second door and in electrical communication with the first biometric scanner.

The kiosk may further include a second biometric scanner within the patient compartment. The first biometric scanner may be in electrical communication with the first lock.

The kiosk may further include a medication container storage compartment accessible through the one-way receptacle; a second door accessible in the patient compartment limits access to the medication container storage compartment; a second lock in mechanical cooperation with the second door; and a second biometric scanner within the patient compartment in electrical communication with the second lock.

A kiosk may be summarized as including a chassis including an external surface and a medication compartment within the chassis; a safe within the medication compartment of the chassis, the safe including: an internal chamber; and a first door that limits access to the internal chamber; and a second door coupled to the chassis limits access to the medication compartment and the first door of the safe.

The chassis may further include a patient compartment separated from the medication compartment.

The kiosk may further include a medication dispense structure extending from the patient compartment to the internal chamber of the safe.

The kiosk may further include a manipulator within the internal chamber of the safe; a temperature adjustment module within the internal chamber of the safe, the temperature adjustment module in fluid communication with an environment external to the safe and the chassis; a medication container storage case within the internal chamber; and a surveillance camera within the internal chamber.

The kiosk may further include a medication container storage case in the internal chamber that stores a plurality of medication containers that contain an opioid addiction treatment medication, the plurality of medication containers including: a first medication container that contains a first dosage amount of the opioid addiction treatment medication; and a second medication container that contains a second dosage amount different from the first dosage amount.

The kiosk may further include a lock in mechanical cooperation with the first door; and a biometric scanner on the external surface of the chassis, the biometric scanner in electrical communication with the lock, the biometric scanner configured to unlock the lock.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A kiosk, comprising:
a chassis including:
an external surface;
a patient compartment within the chassis; and
a medication compartment within the chassis;
a safe in the medication compartment, the safe including:
an first internal chamber within the safe; and
a first door that limits access to the first internal chamber within the safe;
a second door coupled to the chassis, the second door limits access to the medication compartment and the first door of the safe;
a third door coupled to the chassis, the third door limits access to the patient compartment;
a first lock in mechanical cooperation with the first door;
a second lock in mechanical cooperation with the second door; and
an external biometric scanner accessible at the external surface of the chassis and in electrical communication with the first and second locks, the biometric scanner configured to unlock the first and second locks.

2. The kiosk of claim 1, further comprising a wall between the patient compartment and the medication compartment, the wall limits access to the medication compartment and the safe through the patient compartment.

3. The kiosk of claim 2, further comprising:
a dispense structure extending from the patient compartment to the first internal chamber of the safe, the dispense structure including a first end and a second end opposite to the first end, the dispense structure in fluid communication with the first internal chamber through the second end; and
a dispense opening in fluid communication with the patient compartment and in fluid communication with the dispense structure through the first end.

4. The kiosk of claim 1, further comprising:
a surveillance camera within the patient compartment;
a video conference display within the patient compartment;
a thermal imager within the patient compartment;
a dispense structure accessible through the patient compartment, the dispense structure in fluid communication with the patient compartment and the first internal chamber;
a one-way receptacle accessible within the patient compartment;
a speaker within the patient compartment; and
an internal biometric scanner within the patient compartment.

5. The kiosk of claim 4, further comprising:
a fourth door within the patient compartment;
an second internal chamber covered by the fourth door and accessible through the fourth door; and
a third lock in mechanical cooperation with the fourth door.

6. The kiosk of claim 1, further comprising:
a manipulator within the first internal chamber;
a temperature adjustment module within the first internal chamber, the temperature adjustment module in fluid communication with an environment external to the first internal chamber and the chassis;
a medication container storage case within the first internal chamber of the safe; and
a surveillance camera within the medication compartment.

7. The kiosk of claim 6, further comprising:
a medication container camera within the internal chamber;
a label printer within the internal chamber; and
an identification device within the internal chamber.

8. The kiosk of claim 6, further comprising a medication restock drawer accessible through the first door.

9. The kiosk of claim 1, further comprising:
a first surveillance camera within the patient compartment;
a video conference display within the patient compartment;
a thermal imager within the patient compartment;
a dispense structure accessible through the patient compartment, the dispense structure in fluid communication with the patient compartment and the first internal chamber;
a one-way receptacle accessible within the patient compartment;
a speaker within the patient compartment;
an internal biometric scanner within the patient compartment;
a manipulator within the first internal chamber;
a temperature adjustment module within the first internal chamber, the temperature adjustment module in fluid communication with an environment external to the first internal chamber and the chassis;
a medication container storage case within the first internal chamber of the safe; and
a second surveillance camera within the medication compartment.

10. A kiosk, comprising:
a chassis including a patient compartment within the chassis and an external surface;
a first biometric scanner on the external surface of the chassis;
a first camera within the patient compartment;
a video conference display within the patient compartment;
a thermal imager within the patient compartment;
a medication dispense structure accessible in the patient compartment;
a one-way receptacle accessible in the patient compartment; and
a first door coupled to the chassis limits access to the patient compartment;
a medication container storage compartment accessible through the one-way receptacle;
a second door accessible in the patient compartment limits access to the medication container storage compartment;
a second lock in mechanical cooperation with the second door; and
a second biometric scanner within the patient compartment in electrical communication with the second lock.

11. The kiosk of claim 10, wherein the chassis further includes:
a medication compartment separate and distinct from the patient compartment;
a safe in the medication compartment, the safe including an internal chamber communicatively coupled to the patient compartment by the medication dispense structure;
a second door coupled to the chassis limits access to the medication compartment; and
a second lock in mechanical cooperation with the second door and in electrical communication with the first biometric scanner.

12. The kiosk of claim 10, further comprising a second biometric scanner within the patient compartment.

13. The kiosk of claim 10, wherein the first biometric scanner is in electrical communication with the first lock.

* * * * *